United States Patent
Rabiner et al.

(10) Patent No.: US 9,254,195 B2
(45) Date of Patent: Feb. 9, 2016

(54) SYSTEMS AND METHODS FOR JOINT STABILIZATION

(71) Applicant: IlluminOss Medical, Inc., East Providence, RI (US)

(72) Inventors: Robert A. Rabiner, Tiverton, RI (US); Thomas Gausepohl, Marl (DE); Gene P. DiPoto, Upton, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

(21) Appl. No.: 14/550,051

(22) Filed: Nov. 21, 2014

(65) Prior Publication Data

US 2015/0088268 A1    Mar. 26, 2015

Related U.S. Application Data

(60) Division of application No. 13/655,808, filed on Oct. 19, 2012, now Pat. No. 8,936,644, which is a continuation-in-part of application No. 13/553,450, filed on Jul. 19, 2012, now Pat. No. 9,144,442.

(Continued)

(51) Int. Cl.
*A61F 2/30* (2006.01)
*A61B 17/72* (2006.01)
*A61B 17/70* (2006.01)

(52) U.S. Cl.
CPC .............. *A61F 2/30* (2013.01); *A61B 17/7079* (2013.01); *A61B 17/7097* (2013.01); *A61B 17/7275* (2013.01); *A61B 17/7291* (2013.01); *A61F 2002/30583* (2013.01)

(58) Field of Classification Search
CPC .......... A61F 2/30; A61B 17/80; A61B 17/56; A61B 17/72; A61N 1/30; A61N 5/062
USPC ........... 623/17.11–18.11; 606/61, 62, 63, 68, 606/70, 86, 92–94, 105, 190–197, 262, 606/280–298; 604/20–21
See application file for complete search history.

(56) References Cited

U.S. PATENT DOCUMENTS

| | | | |
|---|---|---|---|
| 4,271,839 A | 6/1981 | Fogarty et al. | |
| 4,280,233 A | 7/1981 | Raab | |

(Continued)

FOREIGN PATENT DOCUMENTS

| | | |
|---|---|---|
| DE | 40 28 466 | 3/1992 |
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.

(Continued)

*Primary Examiner* — Yashita Sharma
(74) *Attorney, Agent, or Firm* — Greenberg Traurig, LLP; David J. Dykeman; Roman Fayerberg

(57) ABSTRACT

Photodynamic devices for stabilizing a joint are provided. In some embodiments, a photodynamic joint spacer is provided that includes an expandable member configured for attachment to a bone having an excised region; a formable bar configured for attachment to the bone along at least a portion of the expandable member; and a light-sensitive liquid passed into the expandable member to expand the expandable member, wherein the expandable member is shaped by the formable bar to a shape resembling the excised region of the bone, and wherein the light-sensitive liquid is curable upon exposure to light energy to set the expandable member in the shape resembling the excised region to form a photodynamic joint spacer.

14 Claims, 19 Drawing Sheets

Related U.S. Application Data

(60) Provisional application No. 61/548,945, filed on Oct. 19, 2011, provisional application No. 61/509,459, filed on Jul. 19, 2011, provisional application No. 61/509,314, filed on Jul. 19, 2011, provisional application No. 61/509,391, filed on Jul. 19, 2011.

(56) References Cited

U.S. PATENT DOCUMENTS

| | | |
|---|---|---|
| 4,294,251 A | 10/1981 | Greenwald et al. |
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMicheal et al. |
| 4,888,024 A | 12/1989 | Powlan |
| 4,892,550 A | 1/1990 | Huebsch |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,222,958 A | 6/1993 | Chin |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,376,123 A | 12/1994 | Klaue et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,462,552 A | 10/1995 | Kiester |
| 5,480,400 A | 1/1996 | Berger |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 5,997,570 A | 12/1999 | Ligtenberg et al. |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,077,265 A | 6/2000 | Werding et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,136,011 A | 10/2000 | Stambaugh |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,055 B1 | 7/2002 | Farr et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,482,234 B1 | 11/2002 | Weber et al. |
| 6,485,512 B1 | 11/2002 | Cheng |
| 6,494,883 B1 | 12/2002 | Ferree |
| 6,524,251 B2 | 2/2003 | Rabiner et al. |
| 6,524,313 B1 | 2/2003 | Fassier et al. |
| 6,551,321 B1 | 4/2003 | Burkinshaw et al. |
| 6,551,337 B1 | 4/2003 | Rabiner et al. |
| 6,565,528 B1 | 5/2003 | Mueller |
| 6,579,277 B1 | 6/2003 | Rabiner et al. |
| 6,579,279 B1 | 6/2003 | Rabiner et al. |
| 6,605,056 B2 | 8/2003 | Eidenschink et al. |
| 6,620,185 B1 | 9/2003 | Harvie et al. |
| 6,623,505 B2 | 9/2003 | Scribner et al. |
| 6,632,235 B2 | 10/2003 | Weikel et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Ranucci et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |

(56) References Cited

U.S. PATENT DOCUMENTS

| | | |
|---|---|---|
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,211,121 B1 | 7/2012 | Quinn et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 | 5/2014 | Rabiner et al. |
| 8,764,761 B2 | 7/2014 | Truckai et al. |
| 8,870,965 B2 | 10/2014 | Rabiner et al. |
| 8,906,030 B2 | 12/2014 | Rabiner et al. |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 9,050,079 B2 | 6/2015 | Rabiner et al. |
| 2001/0011174 A1 | 8/2001 | Reiley et al. |
| 2001/0044626 A1 | 11/2001 | Reiley et al. |
| 2002/0032444 A1 | 3/2002 | Mische |
| 2002/0082600 A1 | 6/2002 | Shaolian et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |

(56) References Cited

U.S. PATENT DOCUMENTS

| | | |
|---|---|---|
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271024 A1 | 11/2006 | Gertner et al. |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osorio et al. |
| 2007/0233146 A1 | 10/2007 | Henniges et al. |
| 2007/0239148 A1 | 10/2007 | Scheller |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188805 A1 | 8/2008 | Davies et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburner et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0082504 A1 | 4/2011 | Singhatat et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0218626 A1 | 9/2011 | Krinke et al. |
| 2011/0313356 A1 | 12/2011 | Rabiner et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 99/43266 | 9/1999 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/131999 | 10/2009 |
| WO | WO 2010/050965 | 5/2010 |

(56) References Cited

FOREIGN PATENT DOCUMENTS

| WO | WO 2010/118158 | 10/2010 |
|---|---|---|
| WO | WO 2011/060062 | 5/2011 |
| WO | WO 2011/071567 | 6/2011 |
| WO | WO 2011/162910 | 12/2011 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |
| WO | WO 2014/011669 | 1/2014 |
| WO | WO 2014/100427 | 6/2014 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
PCT International Search Report based on PCT/US10/30275 dated Aug. 11, 2010.
USPTO Office Action in U.S. Appl. No. 12/262,411 mailed Sep. 1, 2010.
USPTO Office Action in U.S. Appl. No. 11/964,370 mailed Dec. 9, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 12/858,924 mailed Oct. 24, 2011.
USPTO Office Action in U.S. Appl. No. 12/755,784 mailed Dec. 23, 2011.
USPTO Office Action in U.S. Appl. No. 12/886,288 mailed Dec. 27, 2011.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
PCT International Search Report based on PCT/US11/66871 dated May 1, 2012.
USPTO Office Action in U.S. Appl. No. 12/756,014 mailed May 11, 2012.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 19, 2012.
Extended European Search Report based on EP 07 75 6016 dated Jul. 18, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/859,680 mailed Jan. 17, 2013.
USPTO Office Action in U.S. Appl. No. 12/756,014 mailed Jan. 22, 2013.
USPTO Office Action in U.S. Appl. No. 13/088,916 mailed Jan. 23, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
Supplemental European Search Report based on EP 08 87 7881 dated May 15, 2013.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.

(56) References Cited

OTHER PUBLICATIONS

USPTO Office Action in U.S. Appl. No. 12/943,544 mailed Sep. 25, 2013.
PCT International Search Report based on PCT/US13/049773 dated Oct. 1, 2013.
USPTO Office Action in U.S. Appl. No. 13/617,557 mailed Oct. 9, 2013.
Extended European Search Report based on EP 10 76 2390 dated Oct. 30, 2013.
USPTO Office Action in U.S. Appl. No. 12/262,370 mailed Nov. 21, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.
USPTO Office Action in U.S. Appl. No. 13/800,518 mailed Jun. 10, 2014.
USPTO Office Action in U.S. Appl. No. 12/262,370 mailed Jun. 26, 2014.
USPTO Office Action in U.S. Appl. No. 13/617,557 mailed Jun. 27, 2014.
USPTO Office Action in U.S. Appl. No. 13/335,110 mailed Jul. 31, 2014.
USPTO Office Action in U.S. Appl. No. 13/616,781 mailed Aug. 26, 2014.
USPTO Office Action in U.S. Appl. No. 13/730,521 mailed Sep. 8, 2014.
USPTO Office Action in U.S. Appl. No. 12/756,014 mailed Oct. 7, 2014.
USPTO Office Action in U.S. Appl. No. 13/553,450 mailed Oct. 24, 2014.
USPTO Office Action in U.S. Appl. No. 13/335,110 mailed Oct. 24, 2014.
USPTO Office Action in U.S. Appl. No. 13/553,247 mailed Dec. 5, 2014.
USPTO Office Action in U.S. Appl. No. 13/553,051 mailed Dec. 23, 2014.
USPTO Office Action in U.S. Appl. No. 12/262,370 mailed Jan. 14, 2015.
USPTO Office Action in U.S. Appl. No. 13/617,557 mailed Jan. 15, 2015.
USPTO Office Action in U.S. Appl. No. 13/335,110 mailed Feb. 9, 2015.
USPTO Office Action in U.S. Appl. No. 13/796,085 mailed Feb. 12, 2015.
USPTO Office Action in U.S. Appl. No. 13/553,051 mailed Mar. 31, 2015.
USPTO Office Action in U.S. Appl. No. 13/553,247 mailed May 1, 2015.
USPTO Office Action in U.S. Appl. No. 13/297,097 mailed May 29, 2015.
USPTO Office Action in U.S. Appl. No. 14/171,036 mailed Jun. 1, 2015.
USPTO Office Action in U.S. Appl. No. 14/164,846 mailed Jun. 4, 2015.
USPTO Office Action in U.S. Appl. No. 13/617,557 mailed Jul. 15, 2015.
USPTO Office Action in U.S. Appl. No. 13/796,085 mailed Jul. 17, 2015.

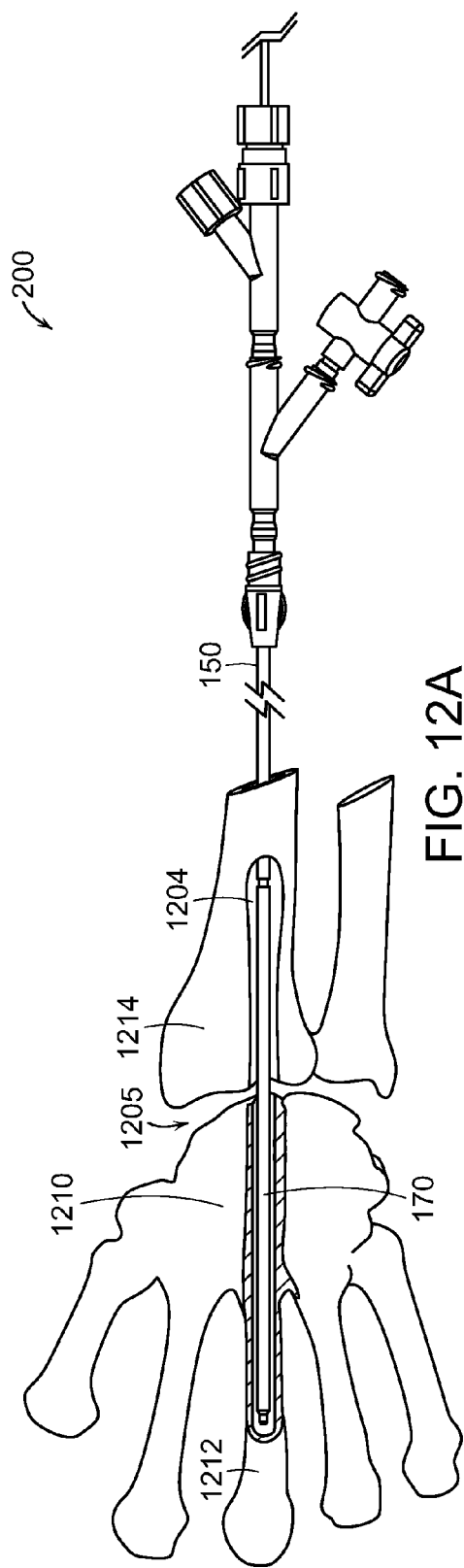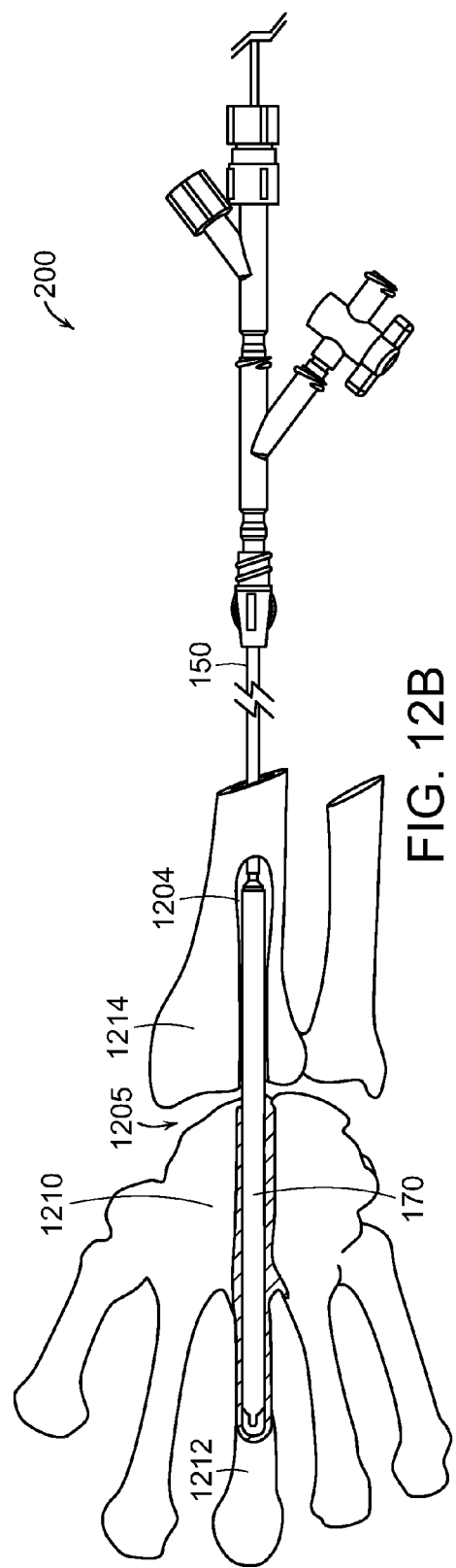

SYSTEMS AND METHODS FOR JOINT STABILIZATION

RELATED APPLICATIONS

This application is a Divisional of U.S. application Ser. No. 13/655,808, filed on Oct. 19, 2012, which claims the benefit of and priority to U.S. Provisional Patent Application No. 61/548,945, filed on Oct. 19, 2011, which U.S. application Ser. No. 13/655,808 is also a continuation-in-part of U.S. application Ser. No. 13/553,450, filed on Jul. 19, 2012, which claims the benefit of and priority to U.S. Provisional Patent Application No. 61/509,459, filed on Jul. 19, 2011, U.S. Provisional Patent Application No. 61/509,314, filed on Jul. 19, 2011, and U.S. Provisional Patent Application No. 61/509,391, filed on Jul. 19, 2011, the entireties of all these applications are hereby incorporated herein by reference.

FIELD

The embodiments disclosed herein relate to bone implants, and more particularly to photodynamic devices for replacement of an articular head of a bone.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align and stabilize the fractured bone. But proper positioning of a bone, particularly in a joint, is difficult to achieve. It would be desirable to have an improved device or method for repairing and positioning a fractured or weakened bone.

SUMMARY

Devices for replacement of an articular head of a bone are provided. In some aspects, there is provided an articular bone repair device including a support member and an articular member. The articular member has an articular part, a bearing surface disposed on the articular part, and an attachment part configured to complementarily engage the support member. The support member is sufficiently designed to reside within a cavity of a bone to anchor the articular member inside the cavity.

In some embodiments, the articular member is fixedly attached to the support member. In some embodiments, the articular member is removably attached to the support member. In some embodiments, the device also includes a recess in the articular member wherein the recess is designed to receive the support member. In some embodiments, the articular member has a shaft and the support member includes an opening into which the shaft of the articular member can be inserted to attach the articular member to the support member. In some embodiments, the articular member has at least a portion that is cylindrical, tubular, rounded or ball-shaped. In some embodiments, the bearing surface is configured to enter into an articular engagement with an articular head of a bone opposing the bone to be repaired. In some embodiments, the support member is curable and/or photodynamic.

In some aspects, a joint repair device includes: a first bone repair device having a first support member attached to a first articular member having a first bearing surface; and a second bone repair device having a second photodynamic support member attached to a second articular member having a second bearing surface complementary to and engaged with the first bearing surface.

In some embodiments, the first articular device and the second articular device are used in conjunction with a complementary surface other than another bone repair device. In some embodiments, the complementary surface is an acetabular cup, a liner, or both. In some embodiments, the first bearing surface is able to articulate with respect to the second bearing surface. In some embodiments, the second bearing surface is able to articulate with respect to first bearing surface. In some embodiments, the first support device is curable and/or photodynamic. In some embodiments, the second support device is curable and/or photodynamic.

In some aspects, a system for restructuring or stabilizing a fractured or weakened head of a bone includes: a delivery catheter having an elongated shaft with a proximal end, a distal end, and a longitudinal axis therebetween, the delivery catheter having an inner void for passing at least one light-sensitive liquid therethrough, and an inner lumen; an expandable member releasably engaging the distal end of the delivery catheter; an articular member attached to the expandable member and having a bearing surface; and a light conducting fiber sized to pass through the inner lumen of the delivery catheter and into the expandable member. The expandable member is configured to receive the articular member. The expandable member moves from a deflated state to an inflated state when the at least one light-sensitive liquid is passed to the expandable member. The expandable member is sufficiently designed to be at least partially placed into a space within the head of the bone. When the light conducting fiber is in the expandable member, the light conducting fiber is able to disperse light energy to initiate hardening of the at least one light-sensitive liquid within the expandable member to form a photodynamic implant. In some embodiments, the articular member has a shaft and the expandable member has an opening configured to receive the shaft of the articular member.

In some aspects, a method for repairing a fractured or weakened articular head of a bone includes: removing the fractured or weakened head from the bone; placing an expandable member removably attached to a distal end of a delivery catheter at least partially into an intramedullary cavity of the bone; attaching an articular member having a bearing surface to the expandable member, wherein the expandable member is configured to receive the expandable member; infusing a light-sensitive liquid into the expandable member through an inner lumen of the delivery catheter; activating a light conducting fiber to cure the light-sensitive liquid inside the expandable member; and separating the expandable member and the articular member from the delivery catheter.

In some embodiments, the method also includes inserting the light conducting fiber into the expandable member. In some embodiments, the method further includes removing the light conducting fiber from the expandable member after curing the light-sensitive liquid inside the expandable member. In some embodiments, the method includes inserting a shaft of the articular member into an opening in the expandable member to attach the articular member to the expandable member.

In some aspects, a kit for repairing or stabilizing a fractured or weakened head of a bone includes: a light conducting fiber; at least one light-sensitive liquid; a delivery catheter having an elongated shaft with a proximal end, a distal end, and a longitudinal axis therebetween; an expandable member releasably engaging the distal end of the delivery catheter, wherein the delivery catheter has an inner void for passing the at least one light-sensitive liquid into the expandable member, and an inner lumen for passing the light conducting fiber into the expandable member; and an articular member configured to be attached to the expandable member and having a bearing surface.

In some embodiments, the kit includes a plurality of expandable members having different sizes or shapes. In some embodiments, the kit includes a plurality of articular members having different sizes or shapes. In some embodiments, the kit includes a light source.

Photodynamic devices for replacement of an articular head of a bone are provided. In one aspect, there is provided an articular photodynamic device that includes a photodynamic support member and an articular member attachable, either fixedly or removably, to the photodynamic support member and having a bearing surface. In some embodiments, the articular member includes a recess designed to receive the photodynamic support member. In some embodiments, the photodynamic support member includes an opening into which a shaft of the articular member can be inserted to attach the articular member to the photodynamic support member.

In some aspects, there is provided a photodynamic joint repair device that includes a first photodynamic bone repair device having a first bearing surface and a second photodynamic bone repair device having a second bearing surface complementary to the first bearing surface. Each of the first and second photodynamic bone repair devices include a photodynamic support member and a articular member having a bearing surface. In some embodiments, an articular photodynamic devices of the present disclosure is used in conjunction with a complementary surface other than another photodynamic bone repair device of the present disclosure, such as for example, an existing acetabular cup and/or liner.

In some aspects, there is provided a device for restructuring or stabilizing a fractured or weakened head of a bone includes a delivery catheter having an elongated shaft with a proximal end, a distal end, and a longitudinal axis therebetween, the delivery catheter having an inner void for passing at least one light-sensitive liquid, and an inner lumen; a expandable member releasably engaging the distal end of the delivery catheter, the expandable member moving from a deflated state to an inflated state when the at least one light-sensitive liquid is passed to the expandable member; wherein the expandable member is sufficiently designed to be at least partially placed into a space within a head of a bone, and a light conducting fiber sized to pass through the inner lumen of the delivery catheter and into the expandable member, wherein, when the light conducting fiber is in the expandable member, the light conducting fiber is able to disperse the light energy to initiate hardening of the at least one light-sensitive liquid within the expandable member to form a photodynamic implant.

In some aspects, there is provided a method for repairing a fractured or weakened articular head of a bone that includes removing the fractured or weakened head of the bone from the bone, placing a expandable member removably attached to a distal end of a delivery catheter at least partially into an intramedullary cavity of the bone, attaching an articular member having a bearing surface to the expandable member, infusing a light-sensitive liquid into the expandable member through an inner lumen of the delivery catheter, inserting a light conducting fiber into the expandable member through an inner void of the delivery catheter, and activating the light conducting fiber to cure the light-sensitive liquid inside the expandable member and separating the expandable member from the delivery catheter.

According to some aspects illustrated herein, there is provided a customizable system for stabilizing an articular joint that includes a light conducting fiber, a delivery catheter having an elongated shaft with a proximal end, a distal end, and a longitudinal axis therebetween, wherein the delivery catheter has an inner void for passing the at least one light-sensitive liquid into a expandable member releasably engaging the distal end of the delivery catheter, and an inner lumen for passing the light conducting fiber into the expandable member, and a formable bar configured to be attached to a bone and to shape the expandable member. In some embodiments, the system for stabilizing an articular joint of the present disclosure is used to stabilize an articular joint following a removal of a failed or infected joint replacement implant.

According to some aspects illustrated herein, there is provided a method for stabilizing an articular joint that includes removing a joint replacement implant and surrounding bone tissues, attaching a formable member to a bone forming the joint, placing a expandable member removably attached to a distal end of a delivery catheter at least partially into an intramedullary cavity of the bone, shaping the formable member to provide the expandable member with an anatomically correct shape, infusing a light-sensitive liquid into the expandable member through an inner lumen of the delivery catheter, inserting a light conducting fiber into the expandable member through an inner void of the delivery catheter, and activating the light conducting fiber to cure the light-sensitive liquid inside the expandable member and separating the expandable member from the delivery catheter to form a photodynamic articulating spacer, removing the formable member, and placing the photodynamic articulating spacer into an anatomically correct position to stabilize the joint until a permanent joint replacement implant can be installed. In some embodiments, the method for stabilizing an articular joint of the present disclosure is used to temporary stabilize an articular joint following a removal of a failed or infected joint replacement implant.

According to some aspects illustrated herein, there is provided a method for performing arthrodesis of a joint that includes drilling a channel between intramedullary cavities of two bones forming a joint, placing a expandable member removably attached to a distal end of a delivery catheter into the channel such that the expandable member transits the joint, infusing a light-sensitive liquid into the expandable member through an inner lumen of the delivery catheter, inserting a light conducting fiber into the expandable member through an inner void of the delivery catheter, and activating the light conducting fiber to cure the light-sensitive liquid inside the expandable member and separating the expandable member from the delivery catheter to form a photodynamic fusion device to stabilize the joint.

According to some aspects illustrated herein, there is provided a photodynamic joint spacer that includes an expandable member configured for attachment to a bone having an excised region; a formable bar configured for attachment to the bone along at least a portion of the expandable member; and a light-sensitive liquid passed into the expandable member to expand the expandable member, wherein the expandable member is shaped by the formable bar to a shape of the excised region of the bone, and wherein the light-sensitive liquid is curable upon exposure to light energy to set the expandable member in the shape of the excised region to form a photodynamic joint spacer.

According to some aspects illustrated herein, there is provided a system for forming a photodynamic joint spacer that includes a delivery catheter having an elongated shaft with a proximal end, a distal end, and a longitudinal axis therebetween, the delivery catheter having an inner void for passing at least one light-sensitive liquid therethrough; an expandable member releasably engaging the distal end of the delivery catheter, the expandable member moveable from a deflated state to an inflated state when the at least one light-sensitive liquid enters the expandable member, wherein the expandable member is sufficiently designed to engage a bone; a formable bar configured for attachment to the bone adjacent the expandable member to shape the expandable member into a desired shape; and a light conducting fiber for providing light energy to the light-sensitive liquid within the expandable member to cure the light-sensitive liquid within the expandable member to set the expandable member in the desired shape to form a photodynamic joint spacer.

According to some aspects illustrated herein, there is provided a method for stabilizing an articular joint that includes attaching a formable bar to a bone in proximity to an excised region; disposing an expandable member adjacent to the formable member; shaping, with the formable bar, the expandable member to approximate an anatomical angle of the excised region of the bone; expanding the expandable member with a light-sensitive liquid; and curing the light-sensitive liquid within the expandable member to create a photodynamic joint spacer having the anatomical angle of the excised region of the bone to stabilize the joint. In some embodiments, to the expandable member to the bone, the expandable member may be inserted into an intramedullary cavity of the bone.

In some embodiments, the formable bar conforms to an outer surface of the bone. In some embodiments, the formable bar is semi-cylindrical for conformal attachment of the formable bar to an outer surface of the bone. In some embodiments, the expandable member is insertable into an intramedullary cavity of the bone. In some embodiments, the expandable member includes an inner lumen which can provide kink resistance to the expandable member. In some embodiments, the inner lumen of the expandable member may be used for insertion of a light conducting fiber into the expandable member for providing light energy to the light-sensitive liquid. In some embodiments, the expandable member is bent by the formable member to a natural angle of the excised region of the bone. In some embodiments, retaining members may be provided for attaching the expandable member to the formable bar.

According to some aspects illustrated herein, there is provided a method for stabilizing an articular joint that includes inserting an expandable member into a cavity through a joint such that a first end of the expandable member is positioned in a first bone on one side of the joint and a second end of the expandable member is inserted into a second bone on the opposite side of the joint; expanding the expandable member with a light-sensitive liquid; and curing the light-sensitive liquid within the expandable member to fuse the joint.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A shows a cross-sectional view of a distal end of the delivery catheter and the expandable member prior to the device being infused with light-sensitive liquid. FIG. 3B shows a cross-sectional view of the distal end of the delivery catheter and the expandable member after the device has been infused with light-sensitive liquid and light energy from the light-conducting fiber is introduced into the delivery catheter and inner lumen of the expandable member to cure the light-sensitive liquid.

FIGS. 12A-12C show an embodiment of method steps for performing arthrodesis of a joint.

Figure 1:
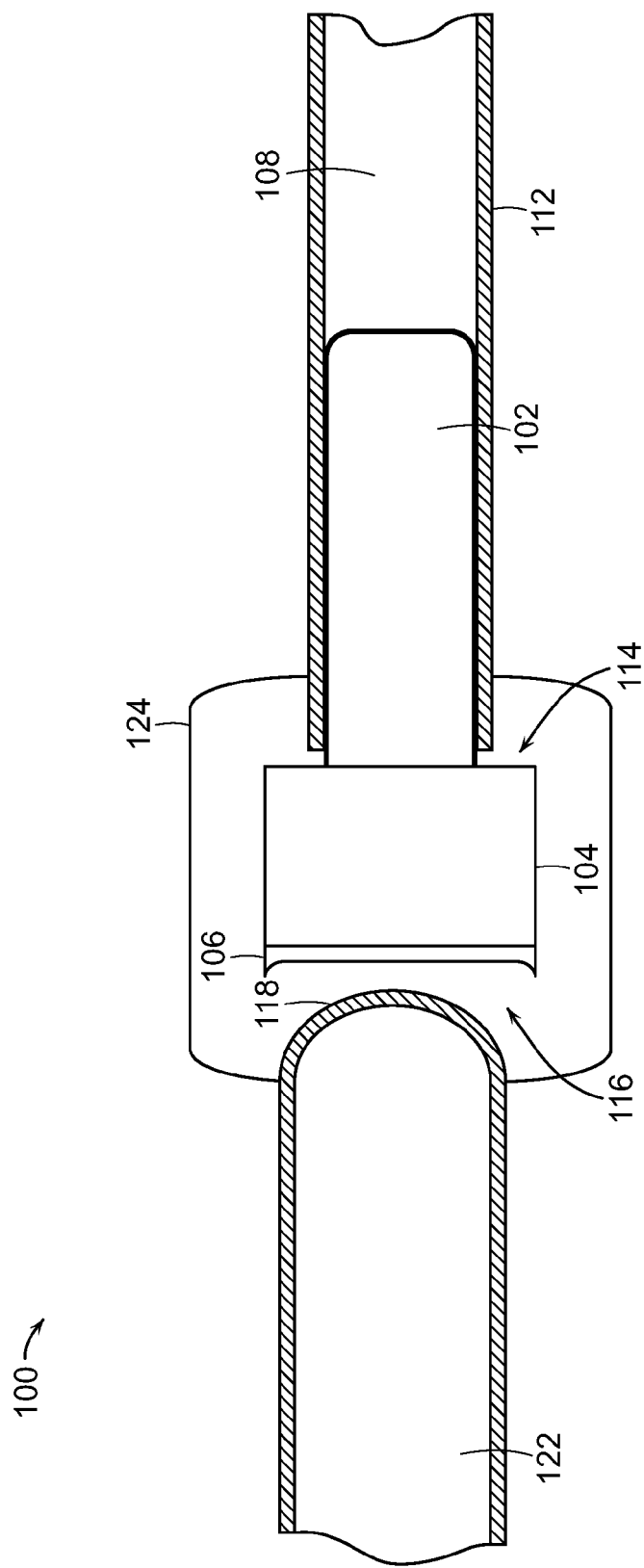
FIG. 1 shows a schematic illustration of an embodiment of an articular photodynamic bone repair device of the present disclosure, including a photodynamic support member and an articular member.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Medical devices and methods for replacing an articular head of a bone are provided. Medical devices and methods for repairing an articular joint are also provided. The term "bone" as used herein refer to an elongated bone having rounded ends, or heads, at its joint with an adjacent bone. The bones include, without limitation, the femurs, tibias, and fibulas of the legs, the humeri, radii, and ulnas of the arms, metacarpals and metatarsals of the hands and feet, the phalanges of the fingers and toes, the spanning or joining of the wrist, the mandible, pelvis, and ribs, and spine. The devices of the present disclosure are suitable for repairing various joints, including, but not limited to, ankle joints, finger joints, toe joints, knee joints, hip joints, wrist joint, elbow joints, mandibular joint, and shoulder joints. In some embodiments, the device is used in a wrist arthrodesis procedure. In some embodiments, an articular joint implant of the present disclosure is used to treat a fractured or weakened bone.

As used herein, the terms "fracture" or "fractured bone" refer to a partial or complete break in the continuity of a bone. The fracture can occur, for example, from an outside force or from a controlled surgical cut (osteotomy). The presently disclosed embodiments can be used to treat any type of bone fracture, including, but not limited to, a displaced fracture, a non-displaced fracture, an open fracture, a closed fracture, a hairline fracture, a compound fracture, a simple fracture, a multi-fragment fracture, a comminuted fracture, an avulsion fracture, a buckle fracture, a compacted fracture, a stress fracture, a compression fracture, spiral fracture, butterfly fracture, other fractures as described by AO Foundation coding, multiple fractures in a bone, and other types of fractures.

As used herein, the term "weakened bone" refers to a bone with a propensity toward a fracture due to a decreased strength or stability due to a disease or trauma. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures may be desirable.

In some embodiments, the devices are used as an interim spacer in a joint such as a hip. For example, the device is used when an implant needs to be removed, an infection subsides, and then an implant is reinserted. Thus, In some embodiments, the device is used to hold the bone (without an implant) in proper spacial alignment, while not being used as a bearing surface.

FIG. 1 illustrates an embodiment of an articular photodynamic bone repair device 100 of the present disclosure for replacing or repairing an articular head of a bone 112. The photodynamic bone repair device 100 includes a photodynamic support member 102 and an articular member 104 attachable, either fixedly or removably, to the photodynamic support member 102 and having a bearing surface 106.

In some embodiments, the photodynamic support member 102 is sufficiently designed to reside within an intramedullary cavity 108 of the bone 112 in order to anchor the articular member 104 inside the intramedullary cavity 108. In some embodiments, the photodynamic support member 102 provides longitudinal and rotational stabilization for the articular member 104. In some embodiments, the photodynamic support member 102 acts to center the articular member 104 inside the intramedullary cavity 108. In some embodiments, the photodynamic support member 102 acts to adjust the angle of the articular member 104 relative to the longitudinal axis of the bone 112. In some embodiments, the photodynamic support member 102 enables the user to adjust the length of the repaired bone to avoid foreshortening of the bone.

The articular member 104 is sufficiently designed to approximate the dimensions and size of an articular head of a bone being repaired. The articular member 104 has any suitable size and shape. In some embodiments, at least a portion of the articular member 104 is roughly cylindrical or tubular in shape. In some embodiments, at least a portion of the articular member 104 is rounded or ball-shaped.

The articular member 104 can be construed of any biologically acceptable material, including, without limitation, a ceramic, plastic, metal or alloy. Suitable metals and metal alloys include, but are not limited to, Nb, Zr, Ti, Ta, Co, V, Cr, Al, alloys thereof, stainless steel, cobalt chrome and combinations thereof. Suitable ceramic materials include, but are not limited to, alumina, zirconia, chromium carbide, chromium nitride, silicon carbide, silicon nitride, titanium carbide, zirconium carbide, zirconium nitride, tantalum carbide, tungsten carbide, and any combination thereof.

The articular member 104 includes an attachment part 114 and an articular part 116. The attachment part 114 is the part of the articular member 116 where the photodynamic support member 102 attaches to the articular member 104. The articular part 116 is the part of the articular member 116 upon which the bearing surface 106 is disposed.

In some embodiments, the bearing surface 106 is configured to approximate the dimensions, size and shape of the bearing surface of an articular head of a bone being repaired. As shown in FIG. 1, the bearing surface 106 is sized and shaped to enter into an articular engagement with an articular head 118 of an opposing bone 122, that is, the bone with which the bone 112 being repaired engages to form an articular joint 124. In some embodiments, the bearing surface 106 is concave. In some embodiments, the bearing surface 106 is flat. In some embodiments, the bearing surface 106 is convex. In some embodiments, the shape of the bearing surface varies along the bearing surface. In some embodiments, the bearing surface 106 is an integral part of the articular member 104. In some embodiments, the bearing surface 106 is a separate part from the articular member 106 and can be attached by any suitable means to the articular part 116 of the articular member 104 either fixedly or removably. For example, the bearing surface can be mounted on the top of an implant (i.e., the head) or affixed to the tip of the implant so that as the curing process occurs, the implant may grab, bond, or attach itself to the bearing surface, such as a metallic stem. In some embodiments, the bearing surface has a screw hole or a compression fitting that is used to attach the articular part of the bearing surface to that of the implant. In some embodiments, the bearing surface 106 is sufficiently designed to withstand the loads and wear on the bearing surface generated by normal activities of the patient post implantation. In some embodiments, the bearing surface 106 is sufficiently designed, i.e., provided with size, shape and material, to ensure low friction between the bearing surface 106 and the articular head 118. The bearing surface 106 may be made of any suitable metallic material, ceramic material, or low-friction plastic, such as polyethylene. The bearing surface 106 can also include a coating designed to decrease friction between the bearing surface of the articular member 10 and the opposing bone.

The photodynamic support member 102 is formed in any suitable manner. For example, as is described in detail below, the photodynamic support member 102 is formed by filling an expandable member 170, such as a balloon, with a photodynamic (light-curable) liquid 165 and exposing the photodynamic (light-curable) liquid 165 to an appropriate frequency of light and intensity to cure the photodynamic liquid 165 inside the expandable member 170 to form a rigid structure within a cavity in a bone, such as the intramedullary cavity 108 (see FIGS. 3A and 3B).

Figure 2:
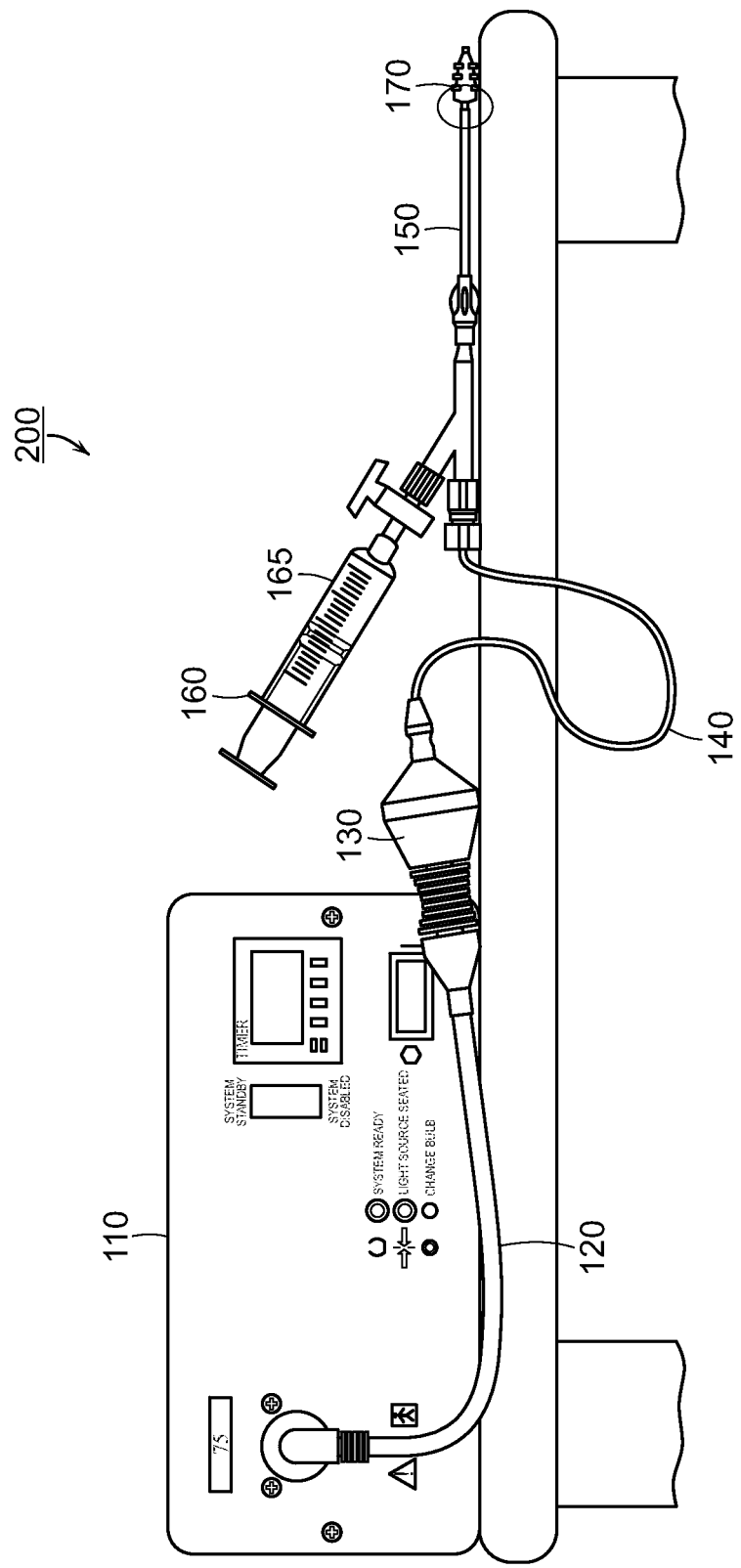
FIG. 2 shows a schematic illustration of an embodiment of a bone implant system of the present disclosure. The system includes a light source, a light pipe, an attachment system, a light-conducting fiber, a light-sensitive liquid, a delivery catheter and a expandable member.
Figure 3A:
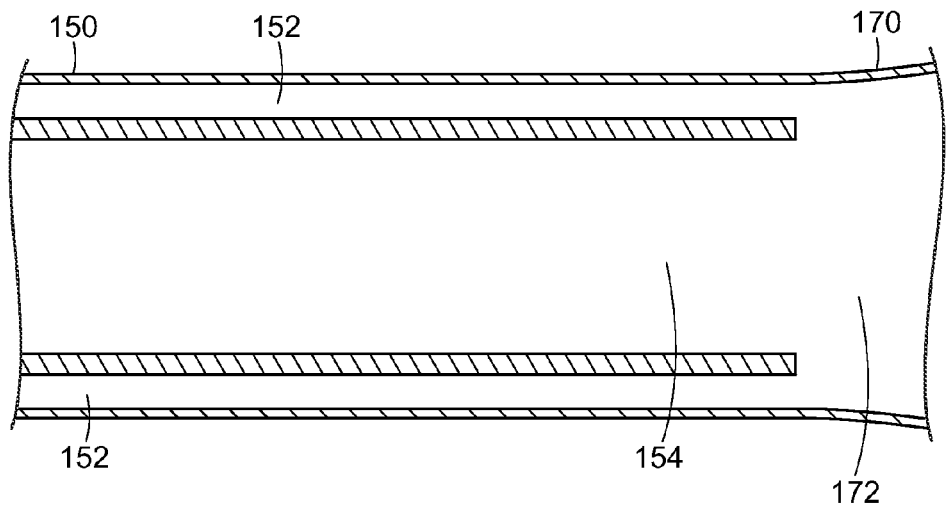
FIG. 3A and FIG. 3B show close-up cross-sectional views of the region circled in FIG. 2.
Figure 3B:
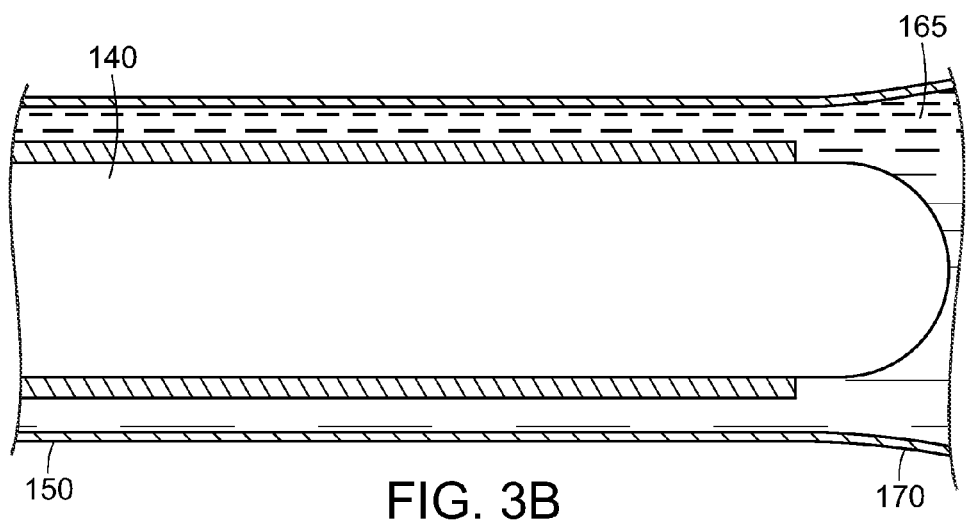
Figure 3C:
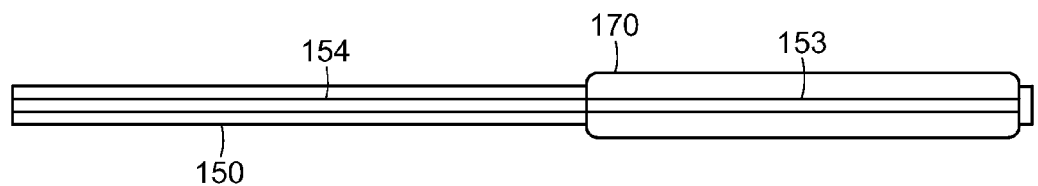
FIG. 3C illustrates a side view of an embodiment of a distal end of the delivery catheter and the expandable member of the present disclosure.

FIG. 2 in conjunction with FIG. 3A, FIG. 3B and FIG. 3C show schematic illustrations of an embodiment of a bone implant system 200 of the present disclosure for formation and implantation of the photodynamic support member 102. System 200 includes a light source 110, a light pipe 120, an attachment system 130 and a light-conducting fiber 140. The attachment system 130 communicates light energy from the light source 110 to the light-conducting fiber 140. In some embodiments, the light source 110 emits frequency that corresponds to a band in the vicinity of 390 nm to 770 nm, the visible spectrum. In some embodiments, the light source 110 emits frequency that corresponds to a band in the vicinity of 410 nm to 500 nm. In some embodiments, the light source 110 emits frequency that corresponds to a band in the vicinity of 430 nm to 450 nm. The system 100 further includes a flexible delivery catheter 150 having a proximal end that includes at least two ports and a distal end terminating in an expandable member 170. In some embodiments, the expandable member 170 is sufficiently shaped to fit within a space or a gap in a fractured bone. In some embodiments, the expandable member 170 is manufactured from a non-compliant (non-stretch/non-expansion) conformable material. In some embodiments, the expandable member 170 is manufactured from a conformable compliant material that is limited in dimensional change by embedded fibers. One or more radiopaque markers, bands or beads may be placed at various locations along the expandable member 170 and/or the flexible delivery catheter 150 so that components of the system 100 may be viewed using fluoroscopy.

In some embodiments, the system includes one or more ports. In the embodiment shown in FIG. 2, the proximal end includes two ports. One of the ports can accept, for example, the light-conducting fiber 140. The other port can accept, for example, a syringe 160 housing a light-sensitive liquid 165. In some embodiments, the syringe 160 maintains a low pressure during the infusion and aspiration of the light-sensitive liquid 165. In some embodiments, the syringe 160 maintains a low pressure of about 10 atmospheres or less during the infusion and aspiration of the light-sensitive liquid 165. In some embodiments, the light-sensitive liquid 165 is a photodynamic (light-curable) monomer. In some embodiments, the photodynamic (light-curable) monomer is exposed to an appropriate frequency of light and intensity to cure the monomer inside the expandable member 170 and form a rigid structure. In some embodiments, the photodynamic (light-curable) monomer 165 is exposed to electromagnetic spectrum that is visible (frequency that corresponds to a band in the vicinity of 390 nm to 770 nm). In some embodiments, the photodynamic (light-curable) monomer 165 is radiolucent, which permit x-rays to pass through the photodynamic (light-curable) monomer 165.

As illustrated in FIG. 3A and FIG. 3B, the flexible delivery catheter 150 includes an inner void 152 for passage of the light-sensitive liquid 165, and an inner lumen 154 for passage of the light-conducting fiber 140. In the embodiment illustrated, the inner lumen 154 and the inner void 152 are concentric to one another. The light-sensitive liquid 165 has a low viscosity or low resistance to flow, to facilitate the delivery of the light-sensitive liquid 165 through the inner void 152. In some embodiments, the light-sensitive liquid 165 has a viscosity of about 1000 cP or less. In some embodiments, the light-sensitive liquid 165 has a viscosity ranging from about 650 cP to about 450 cP. The expandable member 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high pressure delivery is not required, but may be used.

In reference to FIG. 3C, in some embodiments, the expandable member 170 may include an inner lumen in fluid connection with the inner lumen 154 of the delivery catheter 150. In this manner, the light conducting fiber 140 can be passed into the expandable member 170. The inner lumen 153 of the expandable member 170 may be an extension of the inner lumen 154 of the delivery catheter or may be a separate tube in fluid communication with the inner lumen 154 of the delivery catheter.

In some embodiments, a contrast material may be added to the light-sensitive liquid 165 without significantly increasing the viscosity. Contrast materials include, but are not limited to, barium sulfate, tantalum, or other contrast materials known in the art. The light-sensitive liquid 165 can be introduced into the proximal end of the flexible delivery catheter 150 and passes within the inner void 152 of the flexible delivery catheter 150 up into an inner cavity 172 of the expandable member 170 to change a thickness of the expandable member 170 without changing a width or depth of the expandable member 170. In some embodiments, the light-sensitive liquid 165 is delivered under low pressure via the syringe 160 attached to the port. The light-sensitive liquid 165 can be aspirated and reinfused as necessary, allowing for thickness adjustments to the expandable member 170 prior to activating the light source 110 and converting the liquid monomer 165 into a hard polymer.

In some embodiments, the light-sensitive liquid may be provided as a unit dose. As used herein, the term "unit dose" is intended to mean an effective amount of light-sensitive liquid adequate for a single session. By way of a non-limiting example, a unit dose of a light-sensitive liquid of the present disclosure for expanding the expandable member 170 may be defined as enough light-sensitive liquid to expand the expandable member 170 to a desired shape and size. The desired shape and size of the expandable member 170 may vary somewhat from patient to patient. Thus, a user using a unit dose may have excess light-sensitive liquid left over. It is desirable to provide sufficient amount of light-sensitive liquid to accommodate even the above-average patient. In some embodiments, a unit dose of a light-sensitive liquid of the present disclosure is contained within a container. In some embodiments, a unit dose of a light-sensitive liquid of the present disclosure is contained in an ampoule. In some embodiments, the expandable member 170 is sufficiently shaped and sized to fit within a space or a gap in a fractured bone. In some embodiments, the light-sensitive liquid can be delivered under low pressure via a standard syringe attached to the port.

As illustrated in FIG. 2 in conjunction with FIG. 3B, the light-conducting fiber 140 can be introduced into the proximal end of the flexible delivery catheter 150 and passes within the inner lumen 154 of the flexible delivery catheter 150 up into the expandable member 170. The light-conducting fiber 140 is used in accordance to communicate energy in the form of light from the light source to the remote location. The light-sensitive liquid 165 remains a liquid monomer until activated by the light-conducting fiber 140 (cures on demand). Radiant energy from the light source 110 is absorbed and converted to chemical energy to polymerize the monomer. The light-sensitive liquid 165, once exposed to the correct frequency light and intensity, is converted into a hard polymer, resulting in a rigid structure or photodynamic implant of the present disclosure. In some embodiments, the monomer 165 cures in about five seconds to about five minutes. This cure affixes the expandable member 170 in an expanded shape to form a photodynamic implant of the present disclosure. A cure may refer to any chemical, physical, and/or mechanical transformation that allows a composition to progress from a form (e.g., flowable form) that allows it to be delivered through the inner void 152 in the flexible delivery catheter 150, into a more permanent (e.g., cured) form for final use in vivo. For example, "curable" may refer to uncured light-sensitive liquid 165, having the potential to be cured in vivo (as by catalysis or the application of a suitable energy source), as well as to a light-sensitive liquid 165 in the process of curing (e.g., a composition formed at the time of delivery by the concurrent mixing of a plurality of composition components).

Light-conducting fibers use a construction of concentric layers for optical and mechanical advantages. The light-conducting fiber can be made from any material, such as glass, silicon, silica glass, quartz, sapphire, plastic, combinations of materials, or any other material, and may have any diameter, as not all embodiments of the present disclosure are intended to be limited in this respect. In some embodiments, the light-conducting fiber is made from a polymethyl methacrylate core with a transparent polymer cladding. The light-conducting fiber can have a diameter between approximately 0.75 mm and approximately 2.0 mm. In some embodiments, the light-conducting fiber can have a diameter of about 0.75 mm, about 1 mm, about 1.5 mm, about 2 mm, less than about 0.75 mm or greater than about 2 mm as not all embodiments of the present disclosure are intended to be limited in this respect. In some embodiments, the light-conducting fiber is made from a polymethyl methacrylate core with a transparent polymer cladding. It should be appreciated that the above-described characteristics and properties of the light-conducting fibers are exemplary and not all embodiments of the present disclosure are intended to be limited in these respects. Light energy from a visible emitting light source can be transmitted by the light-conducting fiber. In some embodiments, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid.

The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In some embodiments, at least a portion of a length of an light-conducting fiber is modified, e.g., by removing the cladding, in order to alter the profile of light exuded from the light-conducting fiber. The term "profile of light" refers to, without limitation, direction, propagation, amount, intensity, angle of incidence, uniformity, distribution of light and combinations thereof. In some embodiments, the light-conducting fiber emits light radially in a uniform manner, such as, for example, with uniform intensity, along a length of the light-conducting fiber in addition to or instead of emitting light from its terminal end/tip. To that end, all or part of the cladding along the length of the light-conducting fiber may be removed. It should be noted that the term "removing cladding" includes taking away the cladding entirely to expose the light-conducting fiber as well as reducing the thickness of the cladding. In addition, the term "removing cladding" includes forming an opening, such as a cut, a notch, or a hole, through the cladding. In some embodiments, removing all or part of the cladding may alter the propagation of light along the light-conducting fiber. In another embodiment, removing all or part of the cladding may alter the direction and angle of incidence of light exuded from the light-conducting fiber.

In some embodiments, the cladding is removed by making a plurality of cuts in the cladding to expose the core of the light-conducting fiber. In some embodiments, the cladding is removed in a spiral fashion. In some embodiments, the cladding is removed in such a way that a similar amount of light is exuded along the length of the modified section of the light-conducting fiber. In another embodiment, the cladding is removed in such a way that the amount of light exuded along the length of the modified section of the light-conducting fiber changes from the distal end to the proximal end of the modified section. In another embodiment, the cladding is removed in such a way that the amount of light exuded along the modified section of the light-conducting fiber decreases from the distal end of the modified section of the light-conducting fiber toward the proximal end thereof. In some embodiments, to alter the profile of the light exuded from the modified section, the cuts in the cladding are located along the length of the fiber in a spiral. In some embodiments, the pitch or spacing between the cuts is varied along the length of the modified section of the light-conducting fiber. In some embodiments, the spacing between the cuts increases from the proximal end of the modified section of the light-conducting fiber 165 to the distal end thereof such that the amount of light exuded from the modified section of the light-conducting fiber progressively increases toward the distal end of the modified section of the light-conducting fiber.

In some embodiments, the light conducting fiber 140 is part of the delivery catheter 150 or separately placed in the delivery catheter 150. In some embodiments, the light conducting fiber 140 is part of the expandable member 170, or the light conducting fiber 140 is a separate component that is placed in the expandable member 170 before or after the expandable member 170 is inserted into the cavity of the bone.

The expandable member 170 may be provided with a shape demanded by, for example, the anatomy of the implantation site, characteristics of the load bearing member 115 or both. Suitable shapes include, but not limited to, round, flat, cylindrical, dog bone, barbell, tapered, oval, conical, spherical, square, rectangular, toroidal and combinations thereof. In some embodiments, the expandable member 170 is tubular or cone shaped having a substantially centerline opening extending for a length of the expandable member. In some embodiments, the external surface of the expandable member 170 is resilient and puncture resistant. The expandable member 170 can be manufactured from a non-compliant (non-stretch/non-expansion) conformable material including, but not limited to urethane, polyethylene terephthalate (PET), nylon elastomer and other similar polymers. In some embodiments, the expandable member 170 is manufactured from a polyethylene terephthalate (PET). In some embodiments, the expandable member 170 is manufactured from a radiolucent material, which permit x-rays to pass through the expandable member 170. In some embodiments, the expandable member 170 is manufactured from a radiolucent polyethylene terephthalate (PET). In some embodiments, the expandable member 170 is manufactured from a conformable compliant material that is limited in dimensional change by embedded fibers. In some embodiments, at least a portion of the external surface of the expandable member 170 is substantially even and smooth.

In some embodiments, at least a portion of the external surface of the expandable member 170 includes at least one textured element such as a bump, a ridge, a rib, an indentation or any other shape. In some embodiments, at least a portion of the external surface of the expandable member 170 protrudes out to form a textured element. In some embodiments, at least a portion of the external surface of the expandable member 170 invaginates to form a textured element. In some embodiments, the textured element increases the friction and improves the grip and stability of the expandable member 170 after the expandable member 170 is inserted into the fracture location. In some embodiments, the textured element results in increased interdigitation of bone-device interface as compared to an expandable member without textured elements. In some embodiments, the textured element can be convex in shape. In some embodiments, the textured element can be concave in shape. In some embodiments, the textured element can be circumferential around the width of the expandable member 170, either completely or partially.

In general, a bone graft or bone graft substitute can be used in conjunction with an expandable member 170 of the present disclosure. In some embodiments, the bone graft is an allogeneic bone graft. In some embodiments, the bone graft is an autologous bone graft. In some embodiments, the bone graft substitute is a hydroxyapatite bone substitute. In some embodiments, a bone graft or bone graft substitute is used to fill in any gaps that may exist, for example, between the external surface of the expandable member 170 and the surfaces of the bone fragments. In some embodiments, a bone graft or bone graft substitute is used to fill any gaps that may exist, for example, between the textured element of the expandable member 170 and the surfaces of the bone fragments.

In general, the expandable member 170 can include an external surface that may be coated with materials including, but not limited to, drugs (for example, antibiotics), proteins (for example, growth factors) or other natural or synthetic additives (for example, radiopaque or ultrasonically active materials). For example, after a minimally invasive surgical procedure an infection may develop in a patient, requiring the patient to undergo antibiotic treatment. An antibiotic drug may be added to the external surface of the expandable member 170 to prevent or combat a possible infection. Proteins, such as, for example, bone morphogenic protein or other growth factors have been shown to induce the formation of cartilage and bone. A growth factor may be added to the external surface of the expandable member 170 to help induce the formation of new bone. Due to the lack of thermal egress of the light-sensitive liquid 165 in the expandable member 170, the effectiveness and stability of the coating is maintained.

In some embodiments, the expandable member 170 is free of any valves. One benefit of having no valves is that the expandable member 170 may be expanded or reduced in size as many times as necessary to assist in the fracture reduction and placement. Another benefit of the expandable member 170 having no valves is the efficacy and safety of the system 100. Since there is no communication passage of light-sensitive liquid 165 to the body there cannot be any leakage of the light-sensitive liquid 165 because all the light-sensitive liquid 165 is contained within the expandable member 170. In some embodiments, a permanent seal is created between the expandable member 170 and the delivery catheter 150 that is both hardened and affixed prior to the delivery catheter 150 being removed.

In some embodiments, abrasively treating the external surface of the expandable member 170 for example, by chemical etching or air propelled abrasive media, improves the connection and adhesion between the external surface of the expandable member 170 and a bone surface. The surfacing significantly increases the amount of surface area that comes in contact with the bone which can result in a stronger grip.

The expandable member 170 can be infused with light-sensitive liquid 165 and the light-sensitive liquid 165 can be cured to form a photodynamic support member 102, which can then be separated from the delivery catheter 150.

In some embodiments, a separation area is located at the junction between the distal end of the expandable member 170 and the delivery catheter 150 to facilitate the release of the photodynamic support member 102 from the delivery catheter 150. The separation area ensures that there are no leaks of reinforcing material from the elongated shaft of the delivery catheter and/or the photodynamic support member 102. The separation area seals the photodynamic support member 102 and removes the elongated shaft of the delivery catheter by making a break at a known or predetermined site (e.g., a separation area). The separation area may be various lengths and up to about an inch long. The separation area may also have a stress concentrator, such as a notch, groove, channel or similar structure that concentrates stress in the separation area. The stress concentrator can also be an area of reduced radial cross section of cured light-sensitive liquid inside a contiguous cross sectional catheter to facilitate separation by the application of longitudinal force. The stress concentrator is designed to ensure that the photodynamic support member 102 is separated from the delivery catheter 150 at the separation area. When tension is applied to the delivery catheter 150, the photodynamic support member 102 separates from the shaft of the delivery catheter 150, substantially at the location of the stress concentrator. The tension creates a sufficient mechanical force to preferentially break the cured material and catheter composite and create a clean separation of the photodynamic implant/shaft interface. It should of course be understood that the photodynamic support member 102 may be separated from the delivery catheter 150 by any other means known and used in the art, including radial twisting, shear impact, and cross-sectional cutting.

In some embodiments, the shape of the photodynamic support member 102 generally corresponds to the shape of the expandable member 170. Modification of light-sensitive liquid 165 infusion allows a user to adjust the span or thickness of the expandable member 170 to provide specific photodynamic support member 102 size and shape to each subject. In that the expandable member 170 is formable and shapeable by the user prior to the photocuring of the light-sensitive liquid 165 in the expandable member 170, the photodynamic support member 102 best mirrors the size and shape of the area into which it is implanted. In some embodiments, the size and shape of the final photodynamic implant attempts to maximize the surface contact area with the surrounding bone, minimizing specific points of concentrated pressure. In some embodiments, the size and shape of the photodynamic support member 102 attempts to maximize the surface contact area with the surrounding bone, minimizing specific points of concentrated pressure.

Figure 4A:
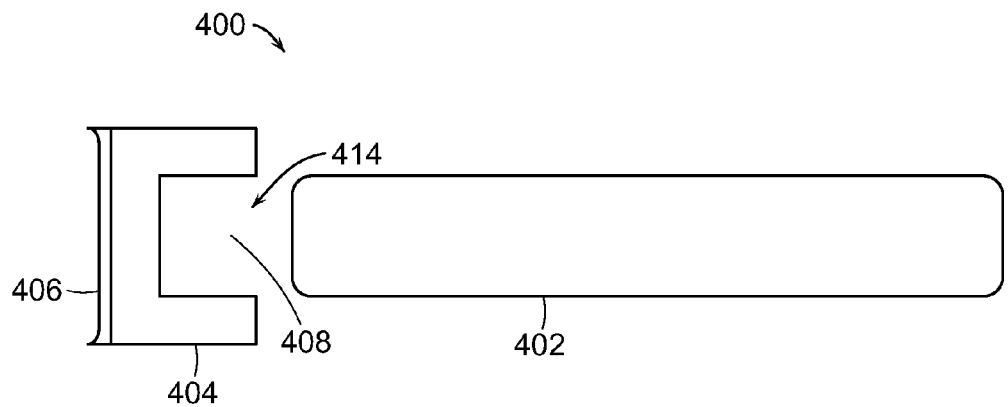
FIGS. 4A-4G illustrate an embodiment of an articular photodynamic device of the present disclosure in which a photodynamic support member is inserted into a recess in an articular member.
Figure 4B:
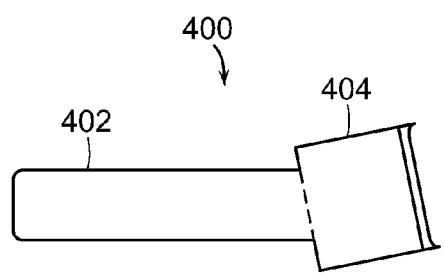
Figure 4C:
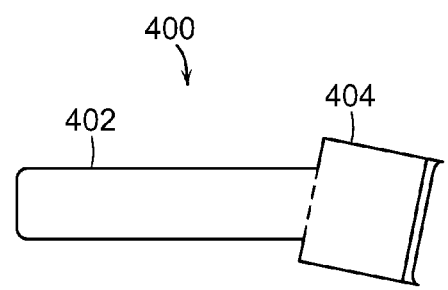
Figure 4D:
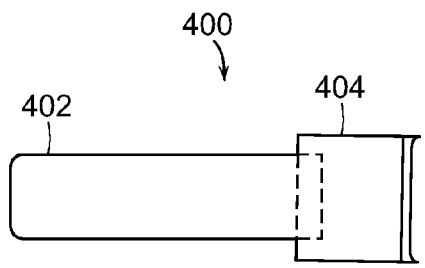
Figure 4E:
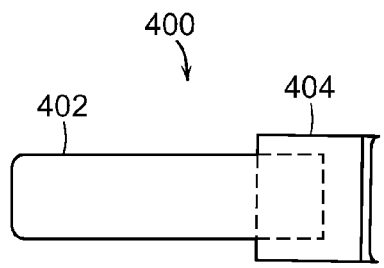

FIG. 4A illustrates an embodiment of an articular photodynamic device of the present disclosure. The articular photodynamic device 400 includes a photodynamic support member 402 and an articular member 404 attachable, either fixedly or removably, to the photodynamic support member portion and having a bearing surface 406. In some embodiments, the articular member 404 attaches to the photodynamic support member 402 at the attachment part 414 of the articular member 404. Any known methods of attachment known in the art and suitable for attaching medical implants may be utilized. In some embodiments, the articular member 404 includes a recess 408 configured to complementarily engage the photodynamic support member 402. The recess 408 is shaped to correspond to the shape of the photodynamic support member 402 so the photodynamic support member 402 can be inserted into the recess 408. The photodynamic support member 402 can be secured within the recess 408 with an adhesive, friction fit, threaded engagement, set screw or a pin, or any other known techniques. In some embodiments, the mechanism of attachment of the photodynamic support member 402 and the articular member 404 is such that, the angle of the articular member 404 relative to the central axis of the photodynamic support member can be adjusted, as shown in FIG. 4B and FIG. 4C. In some embodiments, the articular member 404 is connected to the photodynamic support member 402 at an angle, such as for repair of a head of a humerus or femur. In some embodiments, the height of the implant can also be adjusted by adjusting the depth of engagement between the photodynamic support member 402 and the articular member 404, as shown in FIG. 4D and FIG. 4E.

Figure 4F:
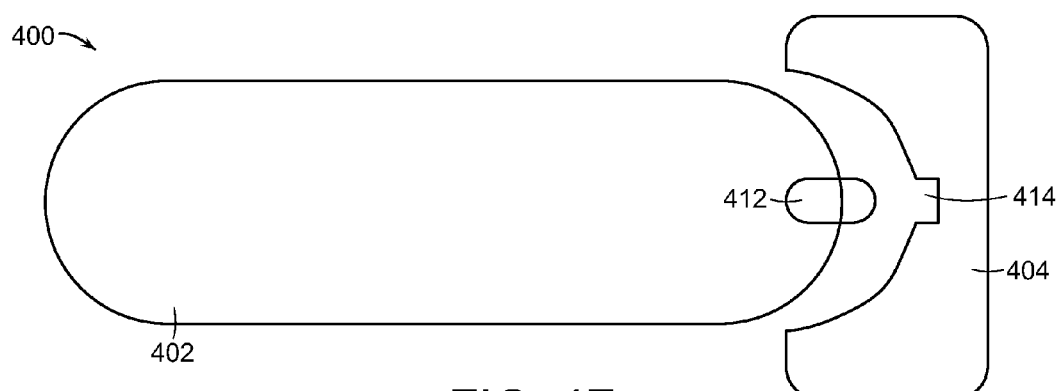
Figure 4G:
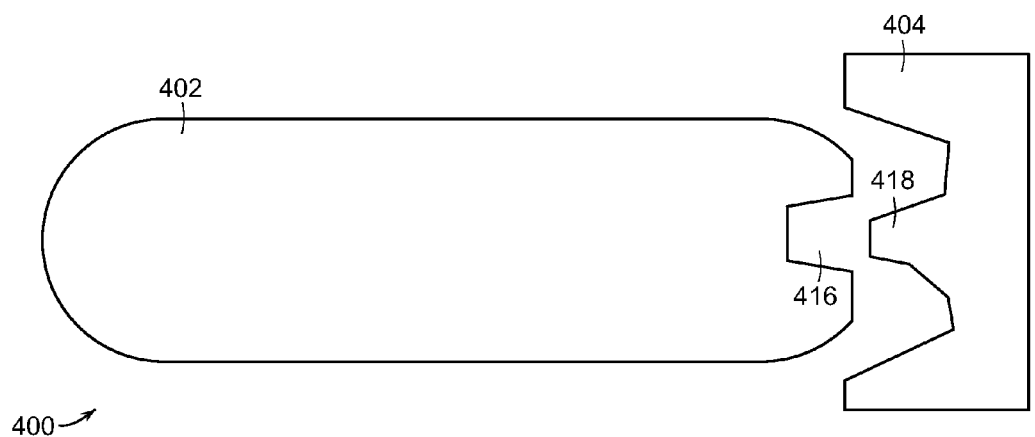

In some embodiments, as shown in FIG. 4F, the photodynamic support member 402 includes a centrator 412, while the articular member 404 includes a centerline recess 414 to assist centering the articular member 404 on the photodynamic support member 402. Alternatively, as shown in FIG. 4G, the photodynamic support member 402 includes a centerline recess 416, while the articular member 404 includes a centrator 418.

Figure 5A:
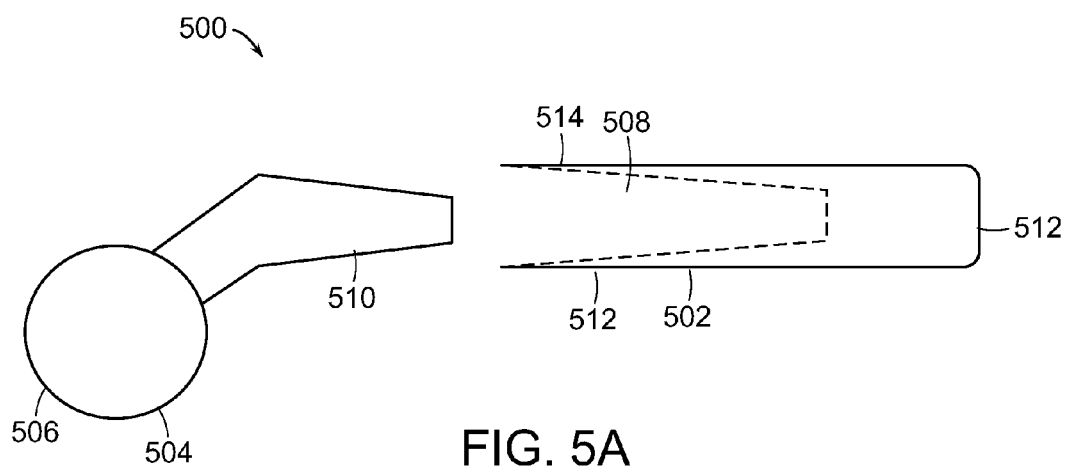
FIG. 5A and FIG. 5B illustrate an embodiment of an articular photodynamic device of the present disclosure in which a photodynamic support member includes a centerline opening for receiving a shaft of an articular member.
Figure 5B:
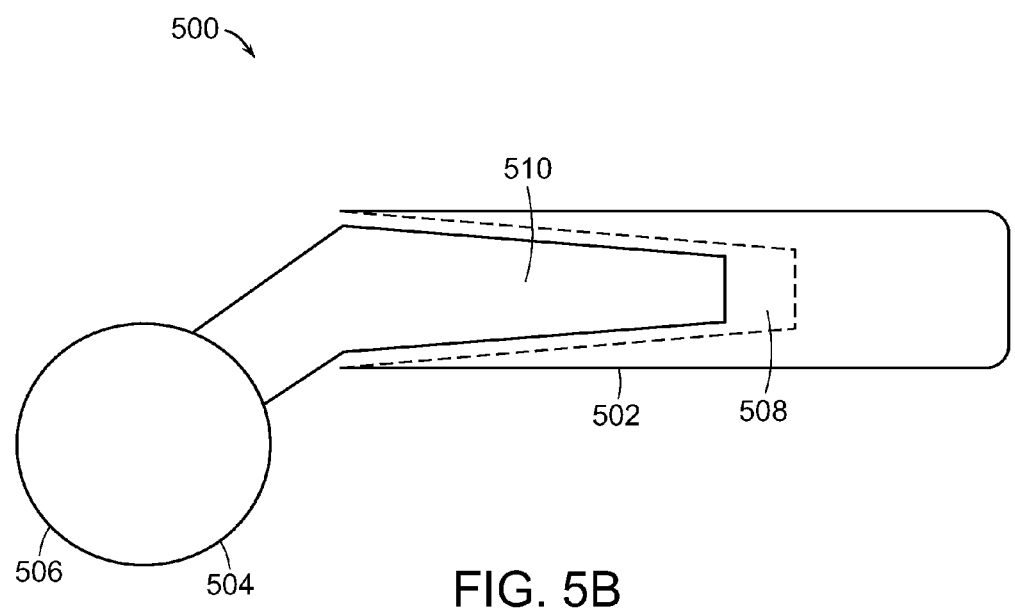

FIG. 5A and FIG. 5B illustrates an embodiment of an articular photodynamic device 500 that includes a photodynamic support member 502 (which, In some embodiments, is made from an expandable member 170 filled with an photodynamic liquid that has been cured in the expandable member 170 to form a rigid structure as discussed above). The articular photodynamic device 500 includes an articular member 504 having a shaft 510. FIG. 5A shows the articular member 504 prior to insertion into the photodynamic support member 502. The articular member 504 is attachable, either fixedly or removably, to the photodynamic support member portion and has a bearing surface 506. In some embodiments, the photodynamic support member 502 includes an opening 508 extending for a length of the photodynamic support member 502 and is designed to receive a shaft 510 of the articular member 504.

FIG. 5B shows an embodiment in which the articular member 502 is inserted into the opening 508 of the photodynamic support member 502. In some embodiments, the opening 508 of the photodynamic support member 502 is uniform throughout the length or the photodynamic support member 502 is tapered. In some embodiments, the opening 502 tapers as the opening 508 extends into the body of the photodynamic support member 502, as shown in FIGS. 5A and 5B. In some embodiments, the opening 508 is open on both sides, i.e., a through-hole extending along the center of the photodynamic support member 502. In some embodiments, the opening 508 is only open on one side of the photodynamic support member 502. In some embodiments, the opening 508 is substantially centered. In some embodiments, the opening 508 can be created by inversion of one end of the balloon (or expandable member 170) toward the opposite end.

In some embodiments, similar to the photodynamic support member 502 shown in FIG. 5A and FIG. 5B, the expandable member 170, from which the photodynamic support member 502 is formed, is tubular or cone shaped having a substantially centerline opening extending for a length of the expandable member. The opening in the expandable member 170 can be uniform throughout the length or may be tapered. In some embodiments, the opening in the expandable member 170 is open on both sides or only open on one side. The delivery catheter 150 can connect to the expandable member 170 either at the base 512 of the expandable member 170 or at one or both legs 514 and 516 of the expandable member 170. In some embodiments, the expandable member 170 includes multiple inner lumens for passing multiple light conducting fibers into each leg 514, 516 of the photodynamic support member 502. Alternatively, the expandable member 170 includes a single inner lumen that is spiral to allow the light conducting fiber to wrap around the opening 508. In such an embodiment, the distal end of the light conducting fiber can be pre-shaped to provide the distal end of the light conducting fiber with a spiral configuration.

The articular photodynamic device 500 also includes an articular member 504 having a shaft 510 designed to be inserted into the opening 510 of the photodynamic support member 502. As the expandable member 170 is infused with the light-sensitive liquid, the articular member 504 is centered in the intramedullary cavity. Curing the light-sensitive material within the expandable member 170 forms the photodynamic support member 502, thereby anchoring the articular member 504 inside the intramedullary cavity and providing longitudinal and rotational stability to the articular member 504. In some embodiments, the shaft 510 of the articular member 504 is secured within the opening 508 in the photodynamic support member 502 by friction fit, set screw, adhesives or any other means known in the art. In some embodiments, the surface of the opening 508 is textured to increase friction between the shaft of the articular member and the photodynamic support member. In some embodiments, the articular member 504 of the articular photodynamic device 500 can be selected from existing joint replacement implants, including, but not limited, to hip replacement implants, knee replacement implants, ankle replacement implants, wrist replacement implants, elbow replacement implants, and shoulder replacement implants. Other joint replacement implants include, for example, mandible, finger and toe implants.

In some embodiments, the photodynamic support member 502 may be formed with a plurality of expandable members 170, where each expandable member 170 can be inflated or deflated independently of other expandable members 170. The individual expandable members 170 can be inflated or deflated as desired to adjust the position, angulation, alignment or combinations thereof of the articular member 504.

Figure 6:
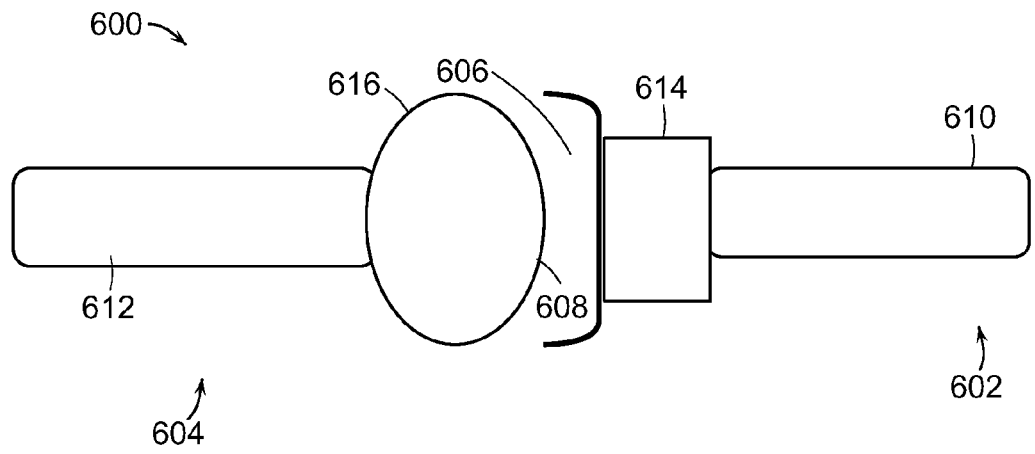
FIG. 6 illustrates an embodiment of a joint repair device of the present disclosure.

In some embodiments, as shown in FIG. 6, there is provided a photodynamic joint repair device 600 that includes a first photodynamic bone repair device 602 having a first bearing surface 606 and a second photodynamic bone repair device 604 having a second bearing surface 608 complementary to the first bearing surface 606. Each of the first and second photodynamic bone repair devices 602, 604 includes a photodynamic support member 610, 612 and an articular member 614, 616 having a bearing surface 606, 608. The first surface 606 and the second surface 608 are sufficiently designed to generally complement one another for an articular engagement. In some embodiments, the first surface 606 and the second surface 608 include one or more corresponding protrusions and channels such that the first surface 606 and the second surface 608 articulate with respect to one another along a predetermined path. In operation, the first photodynamic bone repair device 602 is implanted into one bone forming a joint in need of repair, while the second photodynamic bone 604 repair device is implanted into the other bone or bones of the joint. Once the first photodynamic bone repair device 602 and the second photodynamic bone 604 are implanted into their respective bones, the first bearing surface 606 is engaged with the second bearing surface 608. Because the first bearing surface 606 and the second bearing surface 608 are generally complementary to one another, the first bearing surface 606 and the second bearing surface 608 are able to articulate with respect to one another to imitate natural motion of the joint.

Figure 7:
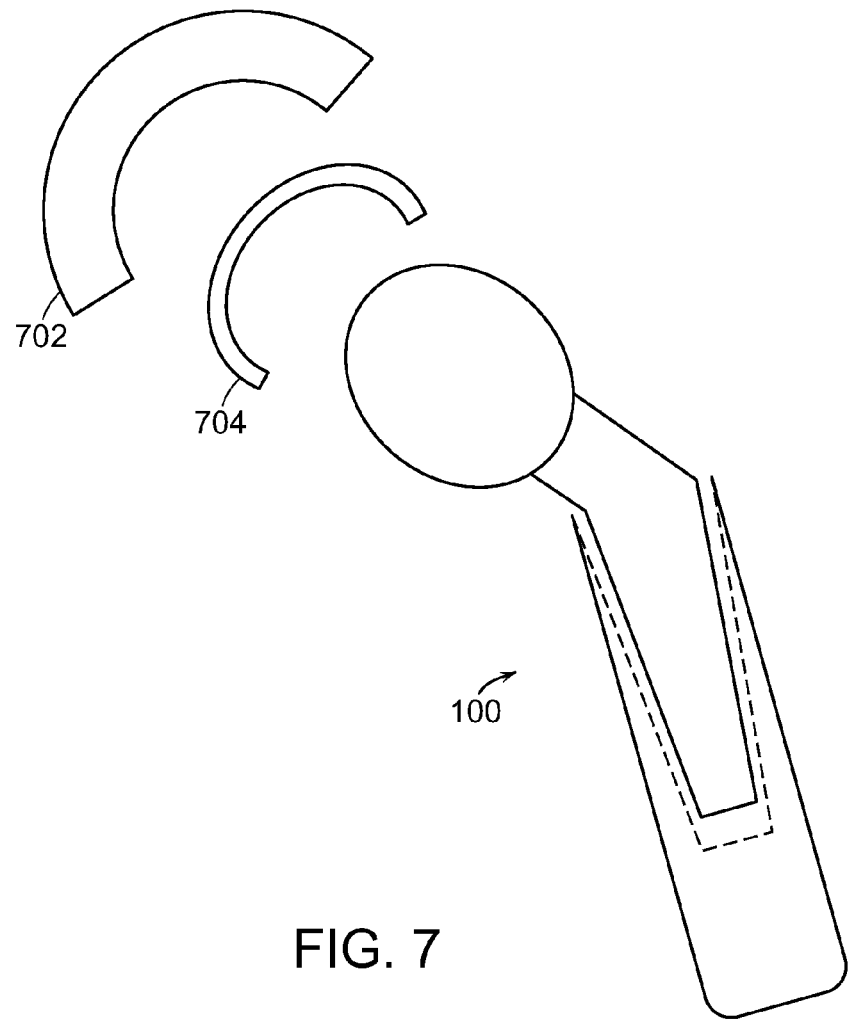
FIG. 7 illustrates another embodiment of a joint repair device of the present disclosure.

In reference to FIG. 7, the articular photodynamic devices 100 can be used in conjunction with a complementary surface other than another photodynamic bone repair device of the present disclosure, such as for example, existing acetabular cups 702 and/or liners 704. Other complementary surfaces include a radial head, shoulder prosthesis, wrist joints, ankle joints, and mandible.

Figure 8A:
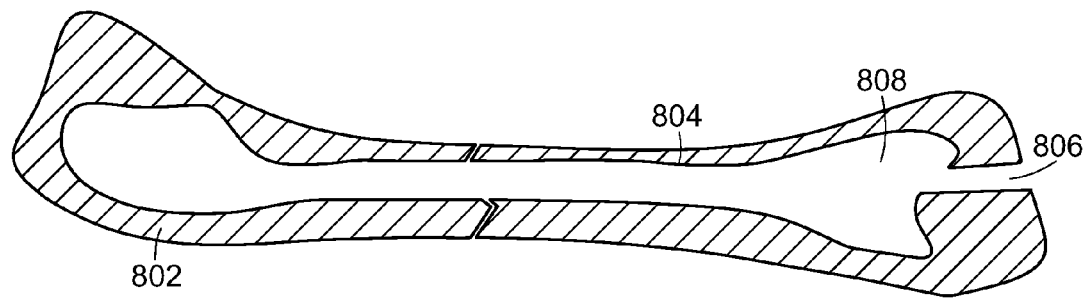
FIG. 8A, FIG. 8B, and FIG. 8C show an embodiment of method steps for using an articular photodynamic device of the present disclosure.

FIGS. 8A-8G illustrate an embodiment of method steps for repairing a fractured or weakened articular head 802 of a bone 804 using an articular photodynamic device of the present disclosure. An incision (not shown) is made through the skin of the patient's body to expose the bone 804. As shown in FIG. 8A, an access hole 806 is formed at the end of the bone 804 opposite the fractured or weakened articular head 802. The access hole 806 can be formed in the bone by drilling or other methods known in the art. The access hole 806 is of any suitable diameter. In some embodiments, the access hole 806 has a diameter of about 3 mm to about 10 mm. In some embodiments, the access hole 806 has a diameter of about 3 mm.

The access hole 806 extends through a hard compact outer layer of the bone 804 into the relatively porous inner or cancellous tissue of an intramedullary cavity 808. For bones with marrow, the medullary material should be cleared from the intramedullary cavity 808 prior to insertion of the inventive device. Marrow is found mainly in the flat bones such as hip bone, breast bone, skull, ribs, vertebrae and shoulder blades, and in the cancellous material at the proximal ends of the bones like the femur and humerus. Once the intramedullary cavity 808 is reached, the medullary material including air, blood, fluids, fat, marrow, tissue and bone debris should be removed to form a void or a hollowed out space within the intramedullary cavity 808. There are many methods for removing the medullary material that are known in the art and within the spirit and scope on the presently disclosed embodiments. Methods include, for example, those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

Figure 8B:
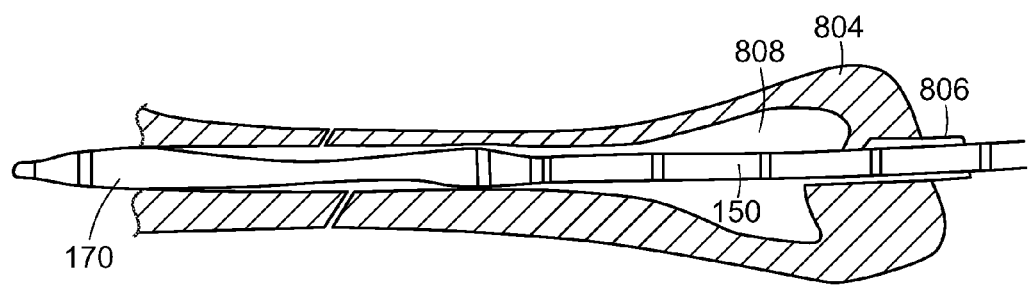

The fractured or weakened articular head 802 (shown in FIG. 8A) is also excised as shown in FIG. 8B.

Next, a guidewire may be introduced into the intramedullary cavity 808 and positioned in the void in the intramedullary cavity 808. As shown in FIG. 8B, an expandable member 170 of an articular photodynamic device of the present disclosure can then be delivered over the guidewire into the void inside the intramedullary cavity 808. In this embodiment, the delivery catheter 150 is connected to the expandable member 170 at the proximal end of the expandable member 170, that is, the end of the expandable member facing the healthy end of the bone 804. In some embodiments, as shown in FIG. 8B, the expandable member 170 can extend for a desired distance outside of the bone 804.

Figure 8C:
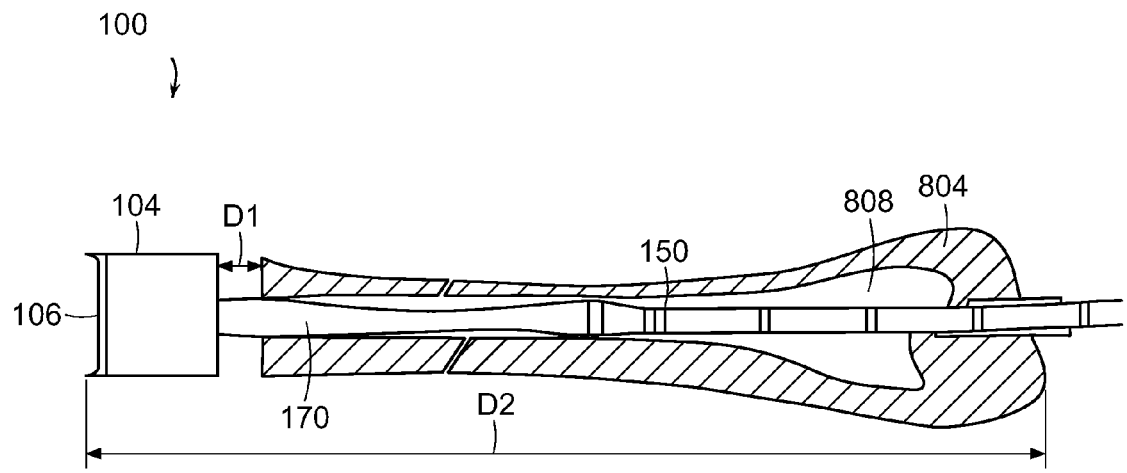

Once the expandable member 170 is in a desired position, the articular member 104 is coupled to the expandable member 170, as shown in FIG. 8C, and placed in a desired position relative to the expandable member 170 similar to the positions shown, for example, in FIGS. 4B-4E with respect to the articular member 404 relative to the photodynamic support member 402 (which is formed from the expandable member 170). The articular member 104 and the expandable member 170 are coupled together in any number of ways and combinations.

Figure 8D:
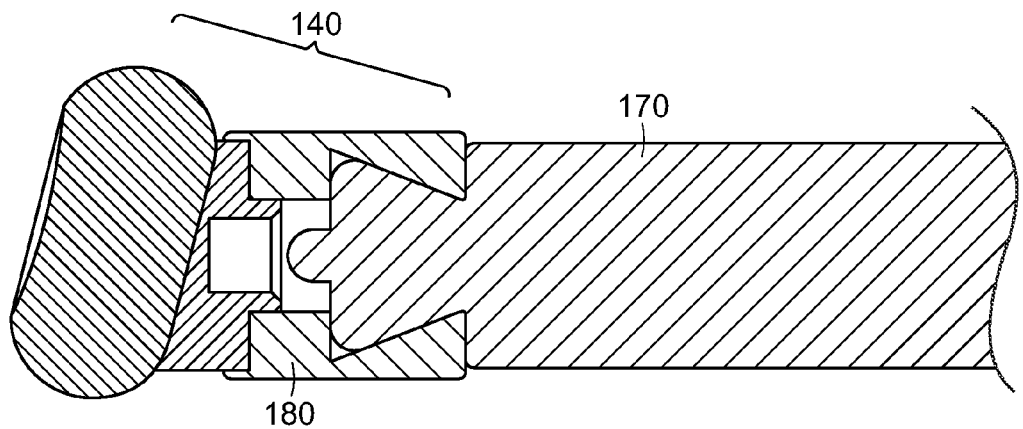
FIG. 8D, FIG. 8E, and FIG. 8F show cross-sectional side views of embodiments of the coupling of the articular member and the expandable member in a radial bone.
Figure 8E:
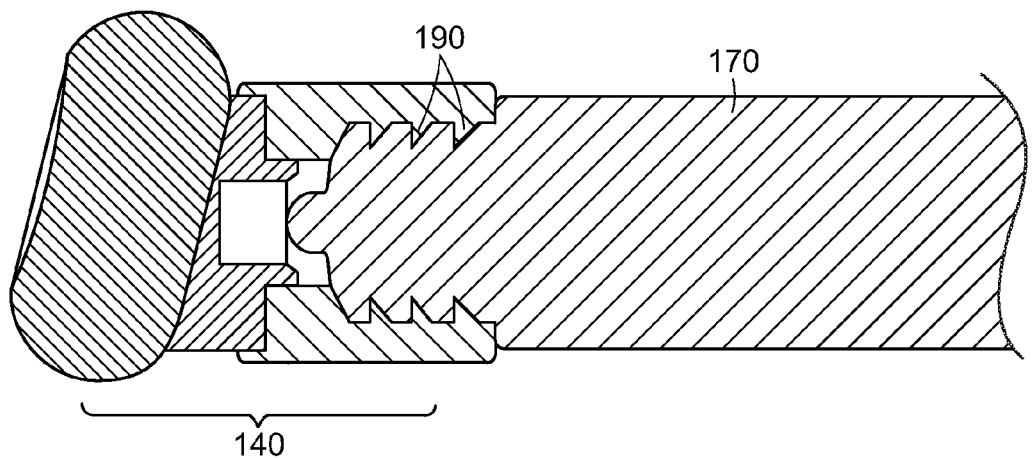
Figure 8F:
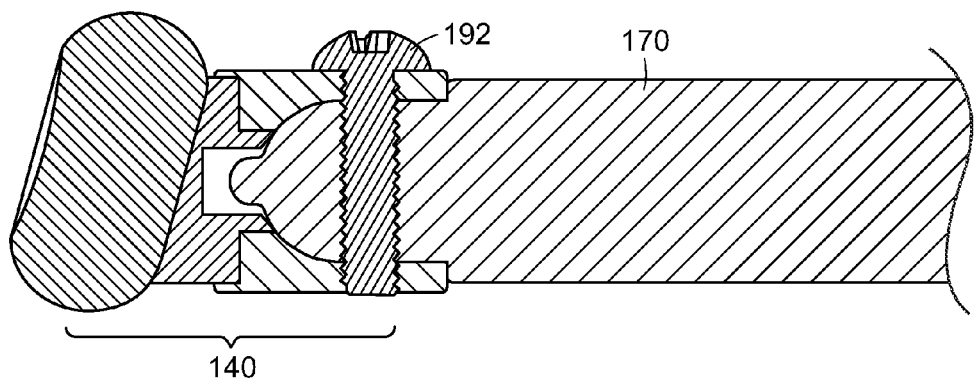

FIG. 8D, FIG. 8E, and FIG. 8F show examples of embodiments of the coupling of the articular member 104 and the expandable member 170 in a radial bone. FIG. 8D shows an undercut 180 where the articular member 140 is coupled to the expandable member 170. When the expandable member 170 expands, the expandable member 170 cannot pull out once cured.

FIG. 8E shows the use of threads or barbs 190 inside the articular member or the sleeve which engage the cured expandable member 170. FIG. 8F shows a bone fixation device 192, such as an externally placed screw or cross-pin, through the coupling of the articular member 140 and the cured expandable member 140. Various other suitable mechanisms may be used to couple the articular member 140 to the expandable member 170.

As explained above, the light-sensitive liquid 165 can then be infused through the inner void in the delivery catheter 150 into the expandable member 170 to move the expandable member from a deflated state to an inflated state. In some embodiments, the expanded expandable member 170 achieves a conformal fit with the intramedullary cavity 808. In reference to FIG. 8C, In some embodiments, a distance D1 between the articular member 104 and the end of the bone 804 can be adjusted by adjusting the length of the expandable member 170 in order to ensure that a length D2 of the repaired bone 804 is substantially the same as the native length of the bone 804.

Figure 8G:
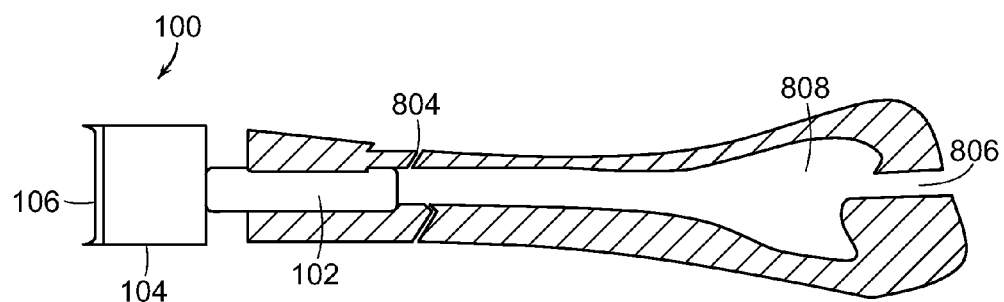
FIG. 8G shows a cross-sectional side view of an embodiment of an articular photodynamic device.

Once the position of the articular member 104 and the fit of the expandable member 170 within the intramedullary cavity 808 is confirmed, the light-sensitive liquid 165 may be hardened within the expandable member 170, such as by illumination with a visible emitting light source (not shown), to form the photodynamic support member 102. After the light-sensitive liquid has been hardened, the light source may be removed from the device. Alternatively, the light source may remain in the expandable member 170 to provide increased rigidity. The photodynamic support member 102 can then be released from the delivery catheter 150 by any known methods in the art, thereby forming an articular photodynamic device 100, as shown in FIG. 8G. In some embodiments, the photodynamic support member 102 achieves a conformal fit with the intramedullary cavity 808 to provide longitudinal and rotational stability to the articular photodynamic device 100.

It should be noted that, In some embodiments, the expandable member 170 can be inserted into the intramedullary cavity 808 through the opening created by excising the fractured or weakened articular head 802. In some embodiments, in order to facilitate setting distance D1 between the articular member 104 and the end of the bone 804, means for limiting the depth of penetration of the expandable member 170 into the intramedullary cavity 808 can be implanted in the intramedullary cavity. In this manner, as the expandable member 170 is expanded in length due to the addition of the light-sensitive liquid 165, the expandable member 170 will be prevented from expanding into the intramedullary cavity, and instead, will expand outside the intramedullary cavity 808. In addition, the articular member 104 may include an opening therethrough to pass the delivery catheter.

Figure 9A:
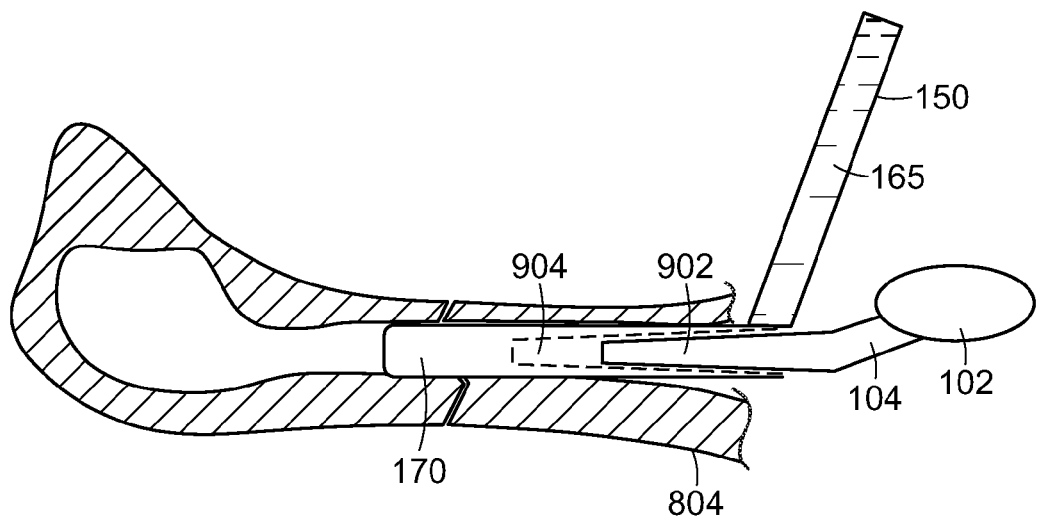
FIG. 9A and FIG. 9B show another embodiment of method steps for using an articular photodynamic device of the present disclosure.
Figure 9B:
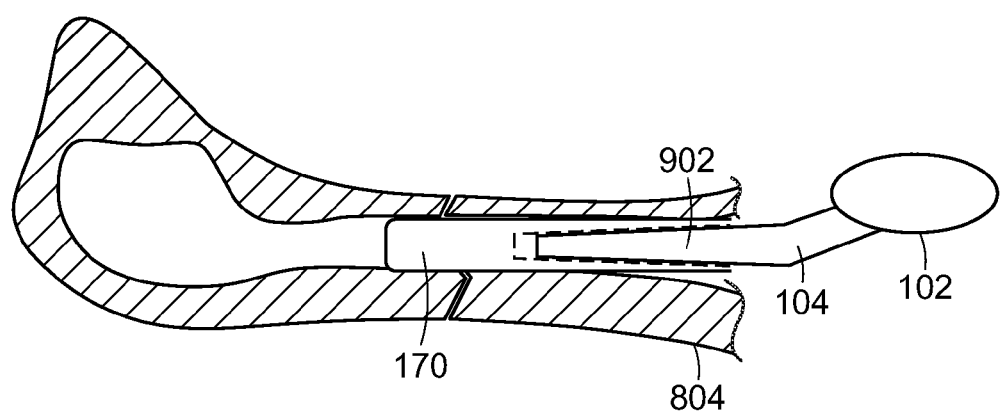

FIG. 9A and FIG. 9B illustrate another embodiment of method steps for repairing a fractured or weakened articular head 802 of a bone 804 in which an articular photodynamic device is inserted through the opening created in the bone by excising a fractured or weakened articular head 802. In this embodiment, the delivery catheter 150 can be connected to the expandable member 170 at the distal end of the expandable member 170, as shown in FIG. 9A. Next, a shaft 902 of the articular member 104 can be inserted into a centerline opening 904 in the expandable member 170 to couple the articular member 104 to the expandable member 170. Next, the expandable member 170 can be infused with a light-sensitive liquid 165. In FIG. 9A, the expandable member 170 has a U-shape with the centerline opening 904. As the expandable member 170 moves from a deflated state to an inflated state, the shaft 902 of the articular member 104 is centered relative to the central longitudinal axis of the bone 804. Thus, the articular member 104 fits within the centerline opening 904 of the expandable member 170. Once the position of the articular member 102 and the fit of the expandable member 170 within the intramedullary cavity 808 is confirmed, the light-sensitive liquid 165 may be hardened within the expandable member 170 to form the photodynamic support member 102, which can then be separated from the delivery catheter 150. FIG. 9B shows the photodynamic support member 102 separated from the delivery catheter 150 after the light-sensitive liquid 165 has hardened within the expandable member 170.

Figure 10A:
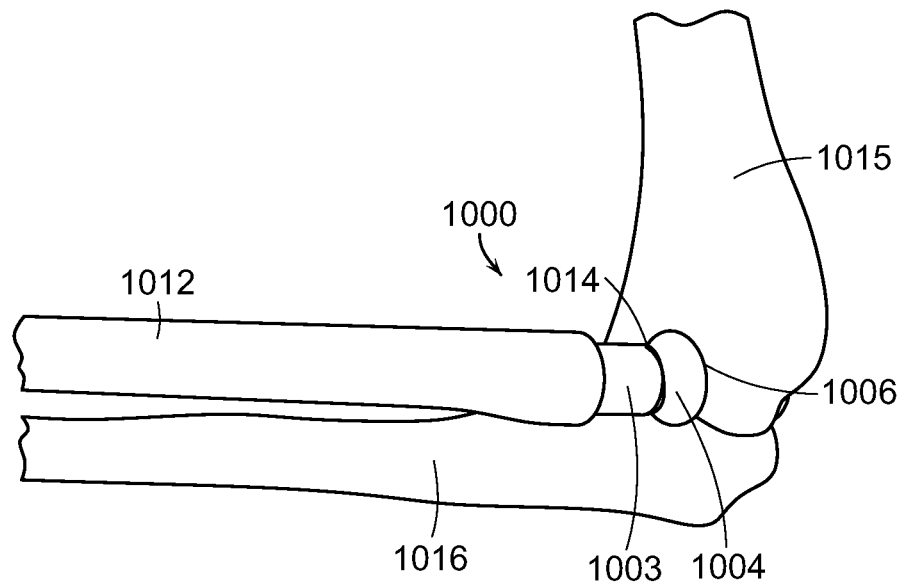
FIG. 10A shows a schematic illustration of an embodiment of an articular photodynamic device of the present disclosure used to replace a proximal head of a humerus.

FIG. 10A shows an embodiment in which an articular photodynamic device 1000 can be used to replace a fractured or weakened proximal head (not shown) of a radius 1012. The fractured or weakened head of the radius 1012 is excised and removed, and the photodynamic support member 1002 (not shown) is formed inside the intramedullary cavity of the radius 1012, as described above. In some embodiments, the photodynamic support member 1002 extends beyond the end of the radius 1012. In some embodiments, the photodynamic support member 1002 is located in the intramedullary cavity of the bone 1012 and extends from the shaft of the bone 1012 through a sleeve 1003 and into the head of the bone 1012.

The articular photodynamic device 1000 also includes an articular member 1004 engaging the photodynamic support member 1002 at the attachment part 1014 of the articular member 1004. The articular member 1004 includes a bearing surface 1006. The articular member 1004 together with the bearing surface 1006 are configured to approximate the dimensions and size of the head of the radius 1012. In some embodiments, the articular member 1004 has a cylindrical form and the bearing surface 1006 is in the form of a shallow concavity or articular engagement with capitellum of the humerus 1015. The deepest point in the bearing surface 1006 is not axi-symmetric with the long axis of the radius 1012, creating a cam effect during pronation and supination. In some embodiments, the circumference of the articular member 1004 is smooth and the articular member 1004 is broad medially where it articulates with the radial notch of the ulna 1016, narrow in the rest of its extent, which is embraced by the annular ligament (not shown). The photodynamic support member 1002 can be illuminated by a light conducting fiber.

As shown in FIG. 10A, In some embodiments, the photodynamic support member 1002 includes a sleeve 1003 that covers the cured expandable member. The sleeve 1003 is engaged with the expandable member by any suitable means. For example, the sleeve 1003 has a plurality of ridges on its inner surface to engage the expandable member and prevent the sleeve 1003 from slipping off the expandable member. In some embodiments, the sleeve has an increasing inner diameter to engage the expandable member and prevent slippage. In some embodiments, the sleeve has an undercut in which the expandable member enters to engage with the sleeve. The sleeve can be cannulated. In FIG. 10A, the sleeve acts as the base of the radial head of the articular photodynamic device 1000. In some embodiments, the sleeve is an anchoring means. In another embodiment, the sleeve is a spacer. The sleeve is of any desired size.

Figure 10B:
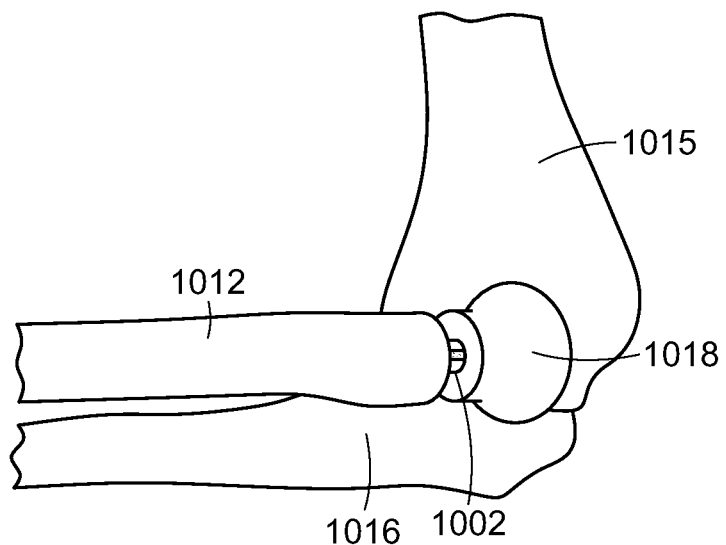
FIG. 10B shows a schematic illustration of an embodiment of an articular photodynamic device of the present disclosure used to repair a proximal head of a humerus.

FIG. 10B shows another embodiment of an articular photodynamic device 1000 that can be used to repair or fixate a fractured or weakened proximal head 1018 of a radius 1012. The fractured or weakened head 1018 of the radius 1012 has not been excised in the embodiment shown in FIG. 10B. The photodynamic support member 1002 is formed inside the intramedullary cavity of the radius 1012, as described above. In some embodiments, the photodynamic support member 1002 extends beyond the end of the shaft of the radius 1012. In FIG. 10B, an expandable member is used to join the fractured head of the bone with the shaft of the bone. The expandable member is inserted into the cavity of the bone and formed into a photodynamic support member 1002 as described above. In FIG. 10B, a space exists between the head 1018 of the joint and the shaft of the bone 1012. In some embodiments, a sleeve is inserted into the space.

In some embodiments, the photodynamic support member 1002 brings the head 1018 and shaft closer together to promote healing of the fractured or weakened bone. In some embodiments, a sleeve is inserted into the space. In some embodiments, the photodynamic support member 1002 brings the head 1018 and shaft into direct contact to promote healing of the fractured or weakened bone.

Although the articular photodynamic implant is described in connection with replacement of a head of a radius, the devices and methods of the present disclosure can also be used to replace a head of other bones, including, without limitation, the femurs, tibias, and fibulas of the legs, the humeri and ulnas of the arms, metacarpals and metatarsals of the hands and feet, the phalanges of the fingers and toes, the clavicles, ankle, wrist, mandible, spinal articular surface bones including, but not limited to, the facet joint and the vertebral body, ribs, temporomandibular joint, and pelvis.

In some embodiments, there is provided a customizable system for stabilizing an articular joint and a method for using the system. In some embodiments, the system and method of the present disclosure can be used to stabilize a joint prior to, or instead of, implanting a permanent joint replacement implant. The system and method of the present disclosure can be used to stabilize a joint following a removal of a joint replacement implant. A joint repair implant may need to be removed or replaced for a variety of reasons. For example, a replacement may be due to an unexpected failure, including a failure caused by an infection or a trauma. On the other hand, the replacement may be due to the normal wear and tear on the implant, such as when the device is implanted into a younger, more active patient. By way of a non-limiting example, when a joint replacement becomes infected, it may loosen, become painful, and need to be removed. Typically, to treat the infection of a joint replacement implant, the existing replacement implant and infected bone tissue, if any, are removed and antibiotics are administered to the patient until the infection is cleared. It is not uncommon to administer antibiotics for six weeks or more before a new joint replacement prosthesis can be implanted. Unless a joint is held in an anatomically correct position during the treatment, the soft tissue (joints, ligaments, muscle) supporting the bones forming the joint may retract or shorten to pull the bones toward one another to decrease the space previously occupied by the joint replacement implant, such that the re-implantation becomes difficult, if not impossible. The presently disclosed embodiments provide a system and method for temporarily filling the space created by the removal of a joint replacement implant to maintain the space and to facilitate re-implantation. In particular, a photodynamic joint spacer is provided that includes an expandable member configured for attachment to a bone having an excised region, a formable bar configured for attachment to the bone along at least a portion of the expandable member and a light-sensitive liquid passed into the expandable member to expand the expandable member. The expandable member may be shaped utilizing the formable bar to a shape of the excised region of the bone. The light-sensitive liquid within the expandable member may be curable upon exposure to light energy to set the expandable member in the shape of the excised region to form a photodynamic joint spacer. The formable bar may also support the expandable member in position as the expandable member is being inflated, as the a light-sensitive liquid is being cured, after the photodynamic joint spacer has been formed, or combination thereof.

Referring to FIGS. 11A-11E, the system 1100 for custom stabilization of an articular joint includes a formable bar 1110 to provide a photodynamic joint spacer 1120 with a desired shape. The formable bar 1110 can be made from stainless steel, titanium, titanium alloy or other biocompatible materials. In some embodiments, the formable bar 1110 may be shaped to substantially conform to the external surface of the bone to which it is attached, such as, for example, in the diaphyseal section of the bone. In some embodiments, the formable bar 1110 may be semi-cylindrical to facilitate conformal attachment of the formable bar 1110 to the bone. The formable bar 1110 may be between about 0.5 mm to about 4 mm thick and between about 1 and about 6 cm wide. The length of the formable bar 1110 may vary widely with the application and patient anatomy. In some embodiments, the formable bar 1110 may be as long as about 30 cm or more in some applications.

Figure 11A:
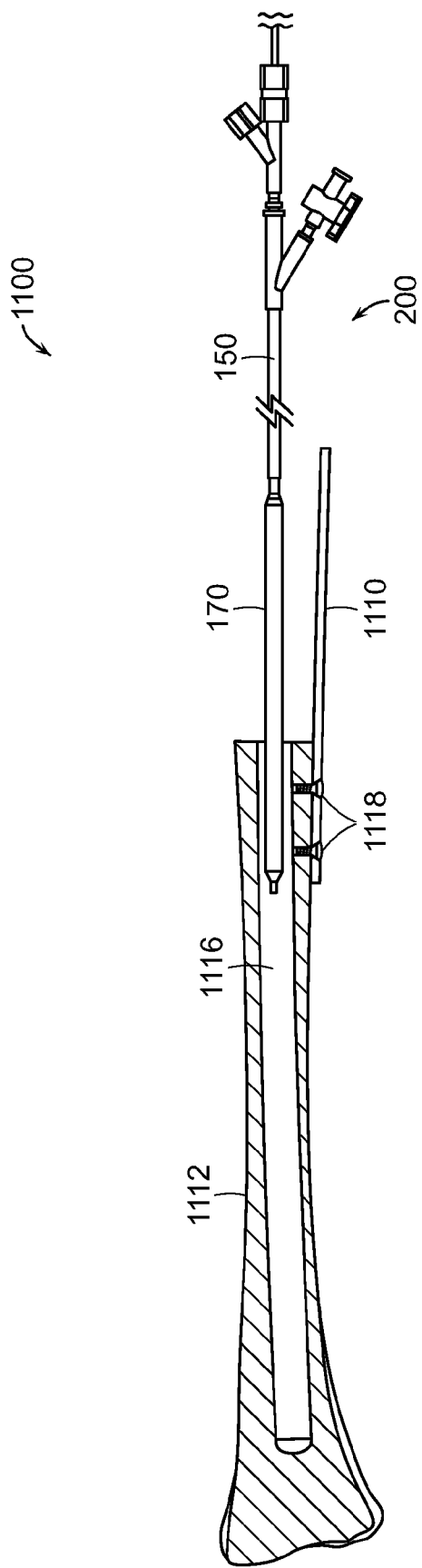
FIGS. 11A-11E show an embodiment of method steps for using a system for stabilizing an articular joint of the present disclosure.

As shown in FIG. 11A, in some embodiments, the formable bar 1110 can be mounted to a bone 1112, which is part of a joint in need of stabilization. While the figures show the formable bar 1110 mounted to the external (periosteal) side of the bone 1112, in some embodiments, the formable bar 1110 can mounted to the internal side of the bone 1112, such as inside the intramedullary cavity 1116 of the bone 1112. The formable bar 1110 can mounted either laterally or medially. In some embodiments, the formable bar 1110 can be removably attached to the bone 1112 using bone screws 1118. In some embodiments, the screws 1118 are placed only on one side of the bone 1112, rather than all the way through the bone 1112.

Figure 11B:
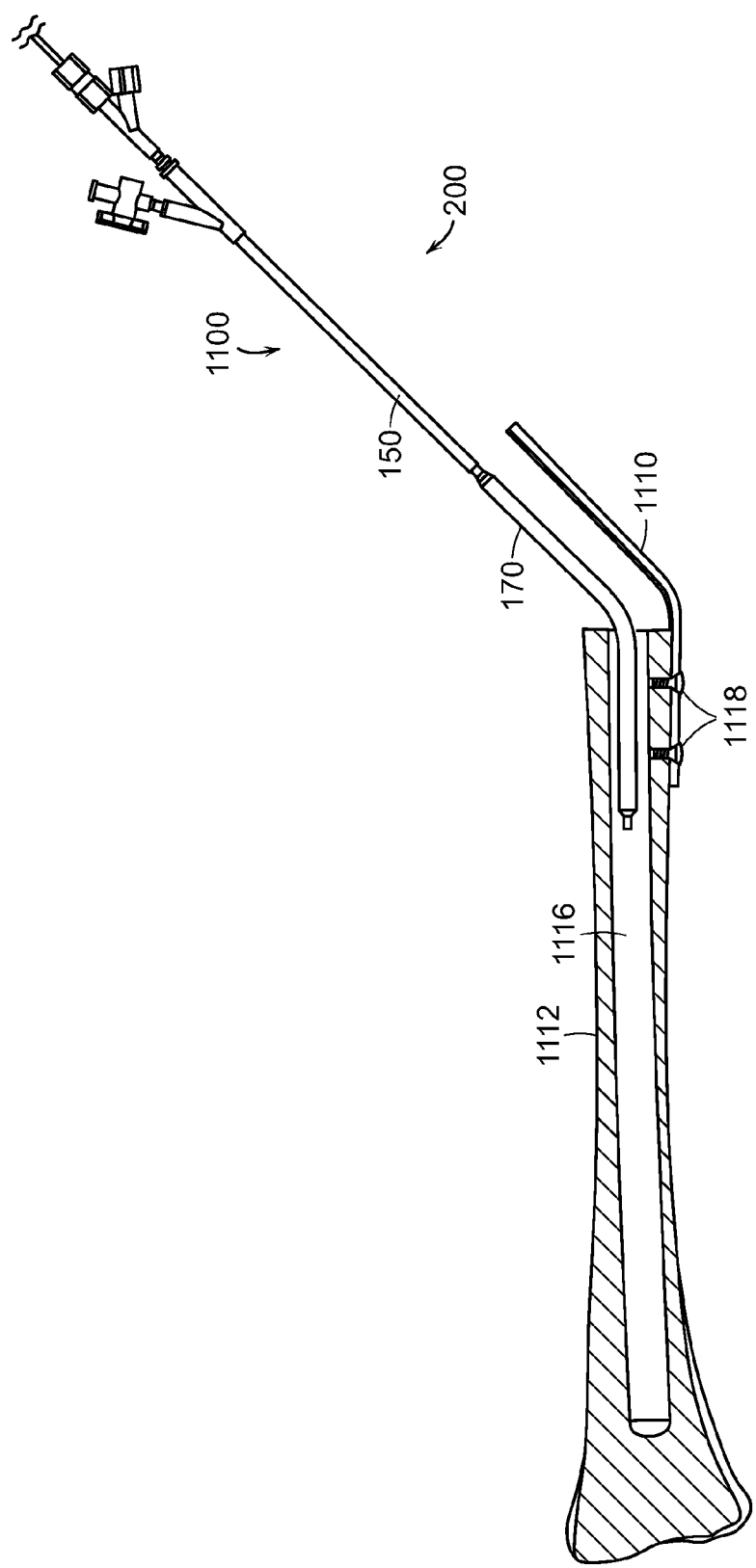

Next, a deflated expandable member 170 is inserted into the intramedullary cavity 1116 of the bone 1112, according to the methods discussed above. As shown in FIG. 11A, the head of the bone 1112 has been excised which enables the insertion of the expandable member 170 into the intramedullary cavity. In some embodiments, the expandable member 170 may have a shape such that the expandable member 170 can be placed over the excised end of the bone 1112, rather than into the intramedullary cavity 1116 of the bone 1112. In some embodiments, the expandable member 170 is part of the bone implant system of the present disclosure. Generally, as shown in FIG. 2 in conjunction with FIG. 3A and FIG. 3B, a bone implant system 200 includes a light source 110, a light pipe 120, an attachment system 130 and a light-conducting fiber 140. The attachment system 130 communicates light energy from the light source 110 to the light-conducting fiber 140. The system 200 further includes a flexible delivery catheter 150 having a proximal end that includes at least two ports and a distal end terminating in an expandable member 170. In some embodiments, the expandable member 170 is sufficiently shaped to fit within a space or a gap in a bone. The expandable member 170 may be moved from a deflated state to an inflated state by infusing a liquid light-sensitive liquid 165 into an inner cavity 172 of the expandable member 170. The light-sensitive liquid 165 can then be exposed to light from the light conducting fiber to harden the expandable member 170 to create a photodynamic joint spacer 1120. As shown in FIG. 11B, the expandable member 170 may be inserted into the intramedullary cavity 1116 only partially such that the distal end of the expandable member extends outside and beyond the intramedullary cavity 1116 parallel to the formable bar 1110.

Figure 11C:
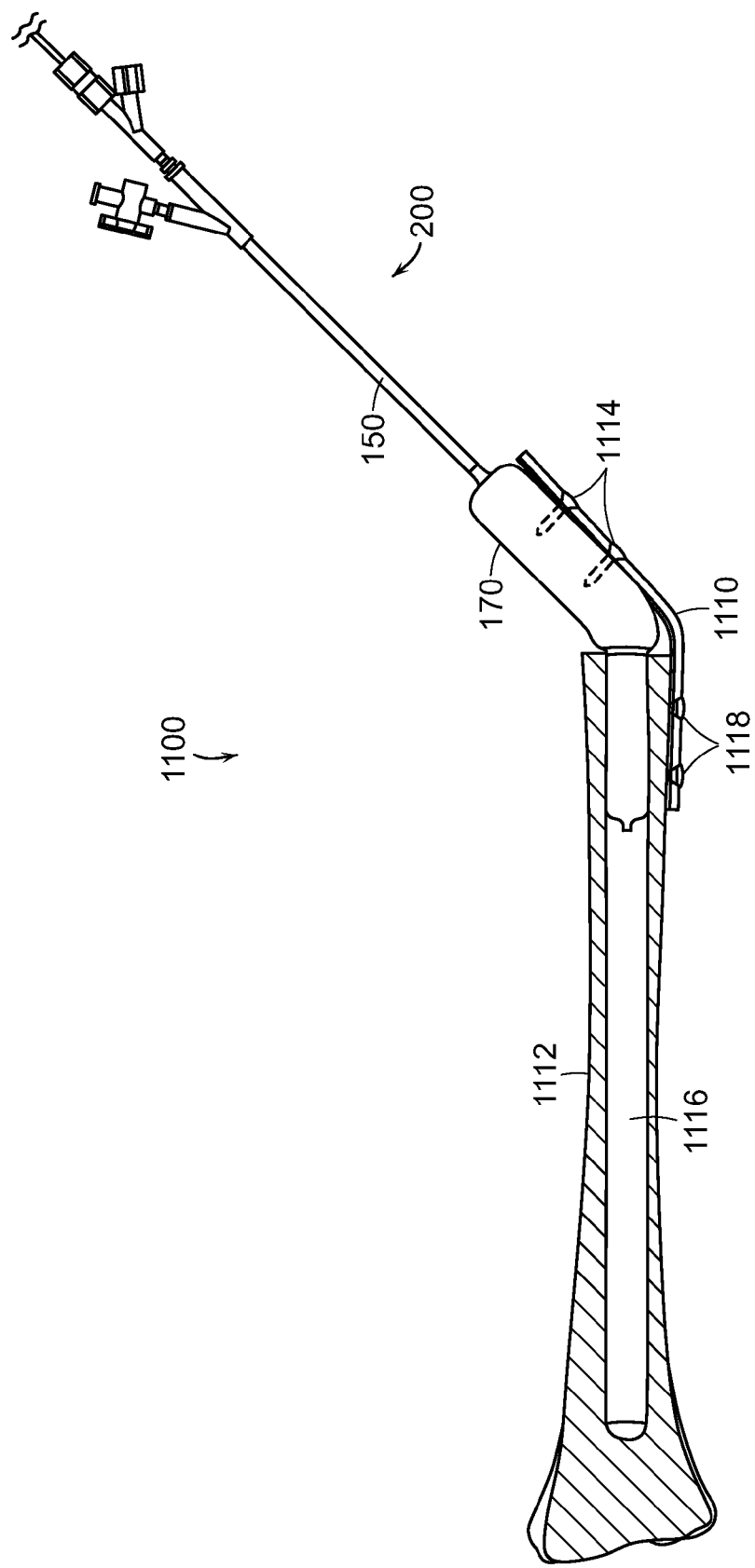

In reference to FIG. 11B, the formable member 1110 is adjacent to the expandable member 170. Because the formable bar 1110 is in contact with the expandable member 170, by shaping the formable member 1110, the expandable member is also shaped. Accordingly, the formable bar 1110 may be shaped or bent to provide the expandable member with a desired shape or angle, which is the shape or angle that can enable the photodynamic joint spacer formed from the expandable member 170 to stabilize the joint in an anatomically correct position. The formable member 1110 may be used to provide the expandable member with a desired angle, tilt, and orientation in relation to the remaining portion of the bone 1112. In some embodiments, the formable member 1110 shapes the expandable member 170 to a shape that resembles the shape of the excised region of the bone. For example, the formable member 1110 is shaped to bend the expandable member 170 to approximate the natural angle of the now-removed neck of the bone 1112, as shown in FIG. 11C. In some embodiments, the expandable member 170 may be shaped so the bend in the expandable member approximates the native angle of inclination of the excised region of the bone 1112. In some embodiments, the expandable member 170 is bent so the end of the expandable member 170 extending away from the bone is at an angle to the longitudinal axis of the bone that approximates the natural angle or angle of inclination of the excised region of the bone 1112. The natural angle of the neck of the bone 1112 may be known from the patient's records or may be estimated by the surgeon during the procedure. It should be noted that, in some embodiments, the formable bar 1110 can be shaped prior to the insertion of the expandable member 170 into the intramedullary cavity 1116. The formable bar 1110 may be shaped so it's approximately parallel to the line that the neck of the bone used to follow before the neck was excised. Once the formable bar 1110 is shaped, the expandable member 170 may be inserted into the intramedullary cavity 1116 and placed along the formable bar 1110 to achieve a desired offset.

In some embodiments, the expandable member 170 may be tubular. In such an embodiment, the formable member 1110 may be placed into the intramedullary cavity 1116 of the bone 1112. In some embodiments, the expandable member 170 may generally have an outer dimension between about 3 mm and about 30 mm. The cross-sectional shape of the expandable member 170 may be constructed to be round or non-round depending on the application. In some embodiments, the cross-sectional shape of the expandable member 170 may be round or oval to match the remaining shape of the shaft of the bone. In some embodiments, the length of the expandable member 170 may be selected depending on the distance required to fill the joint space plus a distance to anchor the expandable member 170 inside the intramedullary canal. Thus the expandable member may be as short as about 3 cm in small bones but as large as about 40 cm in long bones. The expandable member 170 may be flexible along its length and can be configured to bend over small radii without kinking. In some embodiments, as shown in FIG. 3C, the inner lumen 153 of the flexible member 170, which during operation may also contain the light conducting fiber, may keep the expandable member 170 in position and resistant to kinking. In some embodiments, the deflated expandable member 170 may be positioned around the inner lumen 153.

Figure 11D:
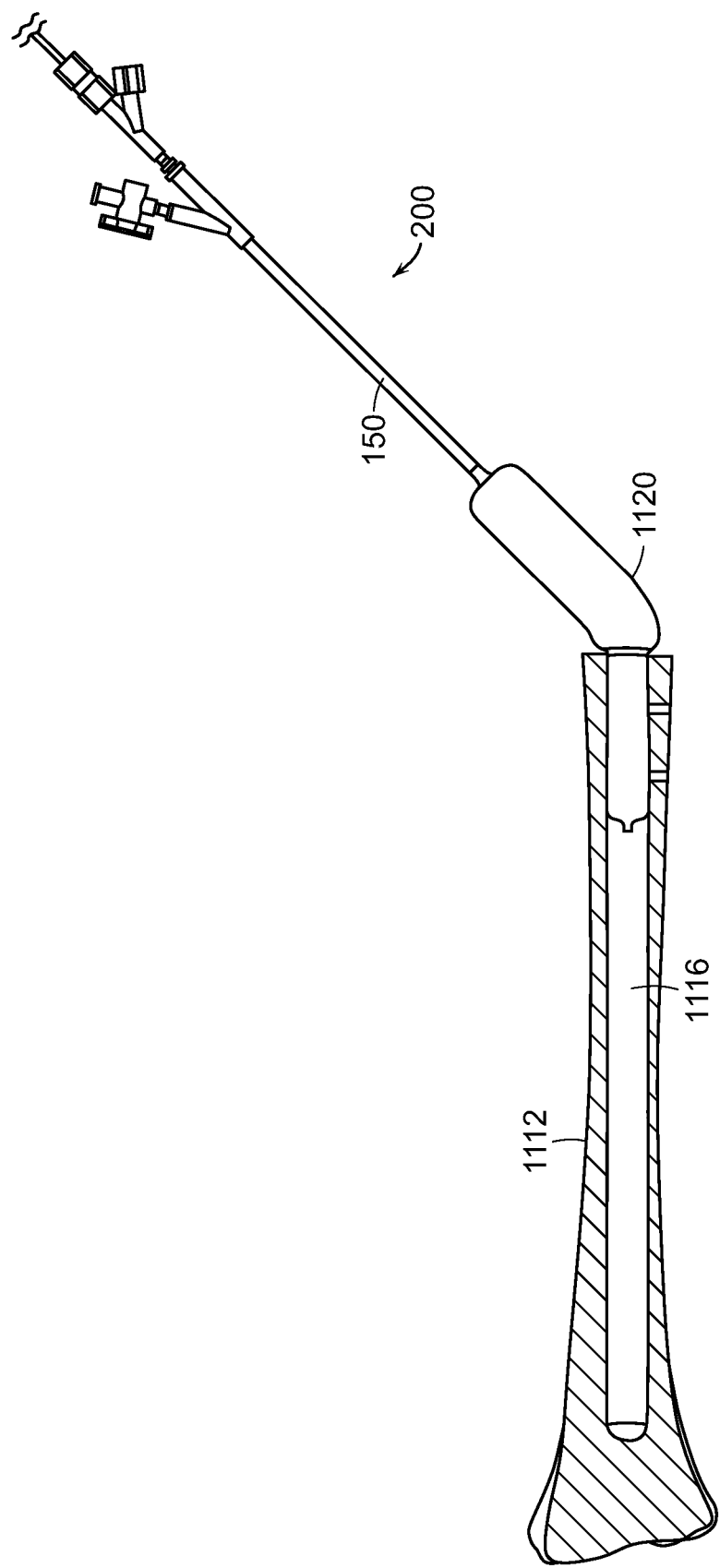
Figure 11E:
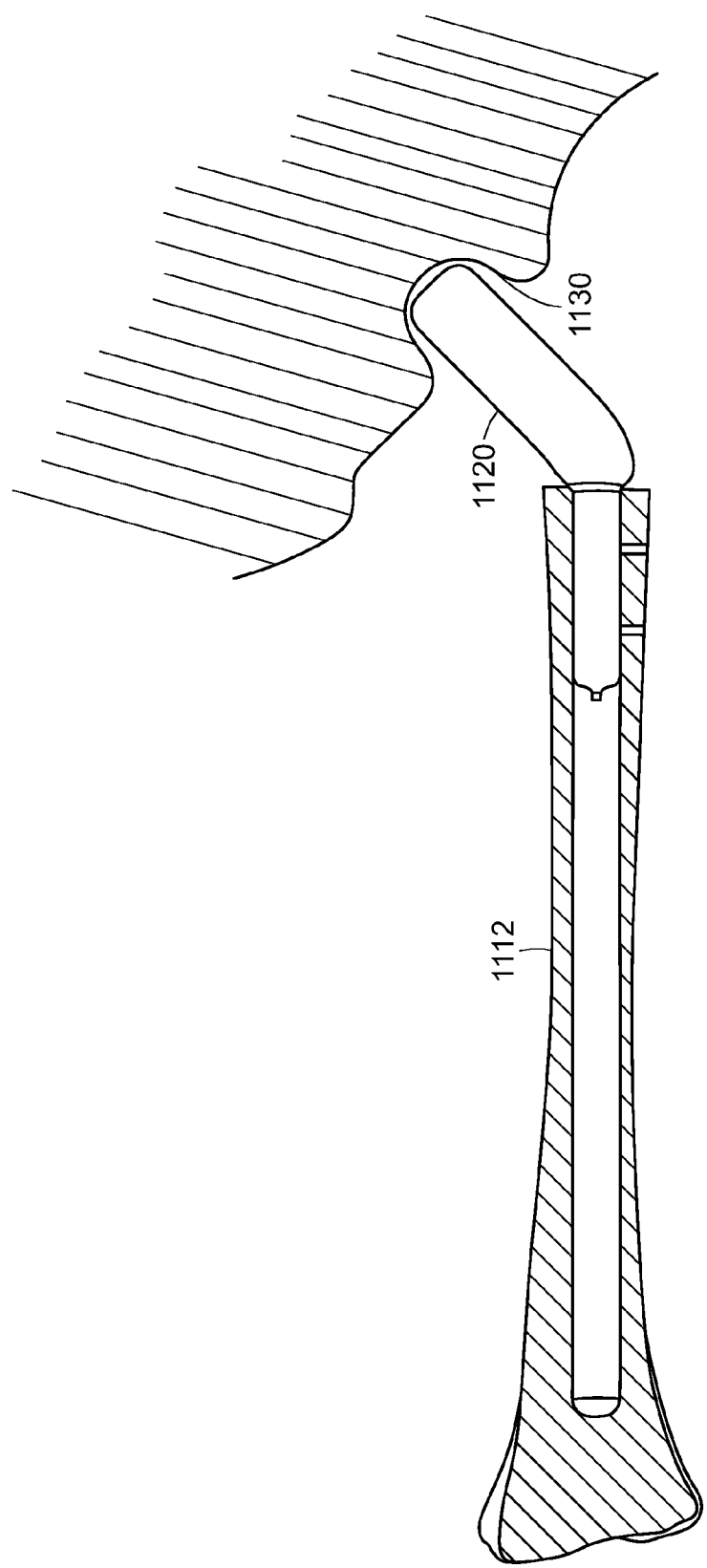

Next, the position of the expandable member 170 may be adjusted to ensure that the joint to be stabilized will be held in the anatomically correct position for a period of time, such as until a new permanent joint replacement implant can be installed. The formable member 1110 supports the expandable member 170 in position as the expandable member 170 is inflated and then later as the light-sensitive liquid inside the expandable member 170 is cured. In some embodiments, the formable bar 1110 is provided with retaining means 1114, such as retaining rings or clips, for attaching, either fixedly or removably, the expandable member 170 to the formable bar 1110. In some embodiments, the retaining means 1114 serve to ensure that the expandable member 170 stays in the desired position, such as parallel to and in contact with the formable bar 1110, during the formation of a photodynamic joint spacer 1120. After the deflated expandable member 170 is provided with a desired off-set position by the formable bar 1110, a light-sensitive liquid is delivered to the expandable member 170 and is cured in the desired off-set position to form a bent photodynamic joint spacer 1120. The angle in the photodynamic joint spacer 1120 mimics the angle of the native neck of the bone to stabilize the joint in a position resembling the native anatomical position of the joint. Once the photodynamic joint spacer 1120 is cured and formed, the formable bar 1110, screws 1118 attaching the formable bar 1110 to the bone 1112, and retaining means 1114 may be removed, as shown in FIG. 11D. In some embodiments, however, the formable bar 1110, screws 1118 attaching the formable bar 1110 to the bone 1112, retaining means 1112 or a combination thereof may be left in place to provide additional support to the photodynamic joint spacer 1120 and the joint. The photodynamic joint spacer 1120 may then be separated from the delivery catheter 150 and may be inserted into the corresponding socket 1130 of the joint, as shown in FIG. 11E. Because the photodynamic joint spacer 1120 is provided with the anatomically-correct length, shape tilt and orientation, the photodynamic joint spacer 1120 can act as a spacer to stabilize the joint in its anatomically-desired position until a permanent implant can be installed, at the appropriate time.

The photodynamic joint spacer of the present disclosure can be used to stabilize various joints, including, but not limited to, ankle joints, finger joints, toe joints, knee joints, hip joints, wrist joints, elbow joints, and shoulder joints. In some embodiments, the photodynamic joint spacer 1120 does not bear load when inserted, and only serves as a spacer to stabilize and temporarily fill the space created by the removal of a joint replacement implant and to preclude the bone from retracting. In some embodiments, the photodynamic joint spacer 1120 can be used to bear load. In some embodiments, the photodynamic joint spacer 1120 can be provided with a bearing surface, as described above, so as to optimize the patient's function while waiting for the implantation of a permanent implant. It should be noted that although the system and method for stabilizing an articular joint has been described in relation to temporarily stabilizing a joint following a removal of a joint replacement device, the presently disclosed systems and methods can be used to implant a new joint replacement device in accordance with the instant disclosure. Moreover, the presently disclosed devices can also be used as permanent implants.

In some embodiments, a system and method for performing arthrodesis of a joint are provided. Arthrodesis is a surgical procedure to fuse the bones that form a joint, essentially eliminating the joint. Arthrodesis is typically performed to relieve intractable pain in a joint which cannot be managed by pain medication or other conservative treatments. The typical causes of such pain are fractures, which disrupt the joint, and arthritis. The systems of the present disclosure may be used to perform arthrodesis on any joint, including, but not limited to, the spine, wrist, finger, ankle, foot, toe, hip, elbow, knee or shoulder joints.

In some embodiments, a bone implant system 200 of the present disclosure for implantation of the photodynamic support member 102 can be used to perform arthrodesis of a joint. Generally, as shown in FIG. 2 in conjunction with FIG. 3A, FIG. 3B and FIG. 3C, the bone implant system 200 includes a light source 110, a light pipe 120, an attachment system 130 and a light-conducting fiber 140. The attachment system 130 communicates light energy from the light source 110 to the light-conducting fiber 140. The system 200 further includes a flexible delivery catheter 150 having a proximal end that includes at least two ports and a distal end terminating in an expandable member 170. In some embodiments, the expandable member 170 is sufficiently shaped to fit within a space or a gap in a bone. The expandable member 170 may be moved from a deflated state to an inflated state by infusing a light-sensitive liquid 165 into an inner cavity 172 of the expandable member 170. The light-sensitive liquid 165 can then be exposed to light from the light conducting fiber to harden the expandable member 170 to create a photodynamic fusion device 1220.

The method for performing arthrodesis of a joint using bone implant system 200 of the present disclosure will now be described in connection with FIGS. 12A-12C. It should be noted that although the method for performing arthrodesis will be described in reference to a wrist joint, these methods are suitable for treating other joints, including, but not limited to, the joints of the spine, finger, wrist, ankle, foot, toe, hip, elbow, knee or shoulder.

In reference to FIG. 12A, to prepare for insertion of the expandable member 170, a channel 1204 transiting a wrist joint is formed. In some embodiments, such channel 1204 may be formed by drilling a hole through a carpal bone 1210 of the wrist joint 1205 and extending into the intramedullary cavity of a metacarpal bone 1212 on one side of the wrist joint 1205 and into the intramedullary cavity of the radius 1214 on the opposite side of the wrist joint. An access hole is also drilled into the intramedullary cavity of the radius 1214 so the expandable member 170 of the system 200 of the present disclosure can be delivered into the channel 1204. The expandable member 170 is inserted in a minimally invasive fashion, using the delivery catheter 150, and is advanced through the intramedullary cavity of the radius 1214 into the channel 1204, such that the expandable member 170 transits the wrist joint 1205, as shown in FIG. 12A.

In reference to FIG. 12B, next, the expandable member 170 can be inflated by delivering the light-sensitive liquid 165 into the expandable member 170. As the expandable member 170 is inflated, the expandable member 170 fills the space in the channel 1204 transiting the wrist joint 1205 and provides alignment and stability to the wrist joint 1205. Moreover, the expandable member 170 may be inflated until the expandable member 170 conforms to the anatomy of the channel 1204 to form a snug fit therein to prevent loosening and/or misalignment of the implant inside the channel.

Figure 12C:
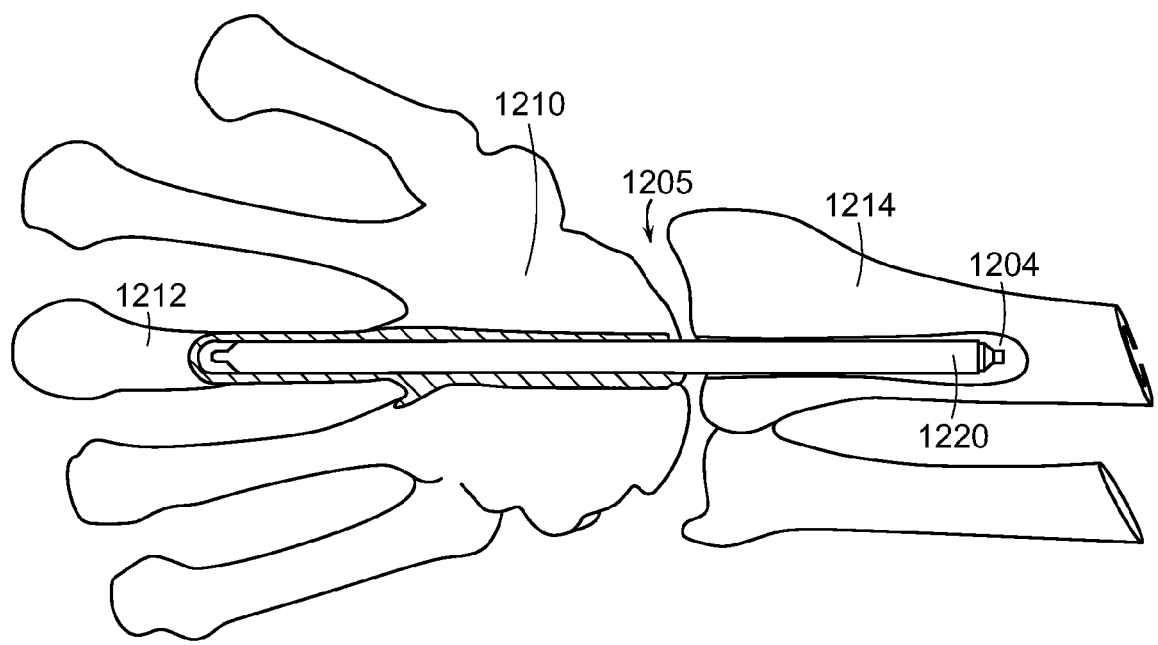

In reference to FIG. 12C, once the expandable member 170 is inflated, the expandable member 170 can be placed into the correct anatomical position by the surgeon prior to curing of the light-sensitive liquid 165 inside the expandable member 170. The position of the joint 1205 may also be adjusted, as necessary. This allows the surgeon to find an optimal position for the expandable member to provide maximum stability and accurate anatomic orientation to the wrist joint 1205. If necessary, the expandable member 170 may be further inflated or deflated to ensure maximum conformance of the expandable member 170 to the internal topography of the channel between the radius 1214 and the metacarpal bone 1212 and to the internal topography of the intramedullary cavities of radius 1214 and the metacarpal bone 1212. When the optimal position and fit for the expandable member 170 are achieved, the light-sensitive liquid 165 within the expandable member is hardened to form the photodynamic fusion device 1220, which can then be separated from the elongated member 150 and left behind in the channel 1204, as shown in FIG. 12C.

In some embodiments, curing of the light-sensitive liquid results in a rigid photodynamic fusion device 1220. In some embodiments, curing of the light-sensitive liquid 165 results in a flexible or bendable photodynamic fusion device 1220. In some embodiments, the light-sensitive liquid 165, when cured, is gel-like, ductile or rubbery, resulting in a photodynamic fusion device 1220 that is flexible or bendable. In some embodiments, the light-sensitive liquid 165, when cured, is semi-hardened, resulting in a photodynamic fusion device 1220 that is flexible or bendable. In some embodiments, the light-sensitive liquid 165, when cured, is malleable, resulting in a photodynamic fusion device 1220 that is flexible or bendable. In some embodiments, the light-sensitive liquid 165 is a multifunctional methacrylate. In some embodiments, the multifunctional methacrylate utilized as the light-sensitive liquid 165 is selected so, when cured, the light-sensitive material 165 can be as rigid or as flexible, as needed for a particular application. In some embodiments, the photodynamic fusion device 1220 of the present disclosure is sufficiently flexible to allow the joint stabilized with the device 1220 to flex. In some embodiments, the photodynamic fusion device 1220 of the present disclosure is sufficiently bendable to allow the joint stabilized with the device 1220 to bend.

In some embodiments, an articular photodynamic device of the present disclosure includes a photodynamic support member and an articular member attachable, either fixedly or removably, to the photodynamic support member portion and having a bearing surface. In some embodiments, the articular member includes a recess designed to receive the photodynamic support member. In some embodiments, the photodynamic support member includes an opening into which a shaft of the articular member can be inserted to attach the articular member to the photodynamic support member.

In some embodiments, a photodynamic joint repair device of the present disclosure includes a first photodynamic bone repair device having a first bearing surface and a second photodynamic bone repair device having a second bearing surface complementary to the first bearing surface, wherein each of the first and second photodynamic bone repair devices include a photodynamic support member and a articular member having a bearing surface.

In some embodiments, a device for restructuring or stabilizing a fractured or weakened head of a bone includes a delivery catheter having an elongated shaft with a proximal end, a distal end, and a longitudinal axis therebetween, the delivery catheter having an inner void for passing at least one light-sensitive liquid, and an inner lumen; a expandable member releasably engaging the distal end of the delivery catheter, the expandable member moving from a deflated state to an inflated state when the at least one light-sensitive liquid is passed to the expandable member; wherein the expandable member is sufficiently designed to be at least partially placed into a space within a head of a bone, and a light conducting fiber sized to pass through the inner lumen of the delivery catheter and into the expandable member, wherein, when the light conducting fiber is in the expandable member, the light conducting fiber is able to disperse the light energy to initiate hardening of the at least one light-sensitive liquid within the expandable member to form a photodynamic implant.

In some embodiments, a method for repairing a fractured or weakened articular head of a bone includes removing the fractured or weakened head of the bone from the bone, placing a expandable member removably attached to a distal end of a delivery catheter at least partially into an intramedullary cavity of the bone, attaching an articular member having a bearing surface to the expandable member, infusing a light-sensitive liquid into the expandable member through an inner lumen of the delivery catheter, inserting a light conducting fiber into the expandable member through an inner void of the delivery catheter, and activating the light conducting fiber to cure the light-sensitive liquid inside the expandable member and separating the expandable member from the delivery catheter.

In some embodiments, a kit for repairing or stabilizing a fractured or weakened head of a bone includes an light conducting fiber, a unit dose of at least one light-sensitive liquid, a delivery catheter having an elongated shaft with a proximal end, a distal end, and a longitudinal axis therebetween, wherein the delivery catheter has an inner void for passing the at least one light-sensitive liquid into a expandable member releasably engaging the distal end of the delivery catheter, and an inner lumen for passing the light conducting fiber into the expandable member, and an articular member configured to engage the expandable member and having a bearing surface. In some embodiments, the kit includes a plurality of expandable members of different sizes or shapes. In some embodiments, the kit includes a plurality of articular members having different sizes or shapes. In some embodiments, the kit includes a light source.

In one aspect, a device for replacement of an articular head of a bone includes a support member and an articular member. The articular member has an articular part, a bearing surface disposed on the articular part, and an attachment part configured to complementarily engage the support member. The support member is sufficiently designed to reside within a cavity of a bone to anchor the articular member inside the cavity.

In one aspect, a joint repair device includes: a first bone repair device having a first support member attached to a first articular member having a first bearing surface; and a second bone repair device having a second photodynamic support member attached to a second articular member having a second bearing surface complementary to and engaged with the first bearing surface.

In one aspect, a system for restructuring or stabilizing a fractured or weakened head of a bone includes: a delivery catheter having an elongated shaft with a proximal end, a distal end, and a longitudinal axis therebetween, the delivery catheter having an inner void for passing at least one light-sensitive liquid therethrough, and an inner lumen; an expandable member releasably engaging the distal end of the delivery catheter; an articular member attached to the expandable member and having a bearing surface; and a light conducting fiber sized to pass through the inner lumen of the delivery catheter and into the expandable member. The expandable member is configured to receive the articular member. The expandable member moves from a deflated state to an inflated state when the at least one light-sensitive liquid is passed to the expandable member. The expandable member is sufficiently designed to be at least partially placed into a space within the head of the bone. When the light conducting fiber is in the expandable member, the light conducting fiber is able to disperse light energy to initiate hardening of the at least one light-sensitive liquid within the expandable member to form a photodynamic implant.

In some aspects, a method for repairing a fractured or weakened articular head of a bone includes: removing the fractured or weakened head from the bone; placing an expandable member removably attached to a distal end of a delivery catheter at least partially into an intramedullary cavity of the bone; attaching an articular member having a bearing surface to the expandable member, wherein the expandable member is configured to receive the expandable member; infusing a light-sensitive liquid into the expandable member through an inner lumen of the delivery catheter; activating a light conducting fiber to cure the light-sensitive liquid inside the expandable member; and separating the expandable member and the articular member from the delivery catheter.

In some aspects, a kit for repairing or stabilizing a fractured or weakened head of a bone includes: a light conducting fiber; at least one light-sensitive liquid; a delivery catheter having an elongated shaft with a proximal end, a distal end, and a longitudinal axis therebetween; an expandable member releasably engaging the distal end of the delivery catheter, wherein the delivery catheter has an inner void for passing the at least one light-sensitive liquid into the expandable member, and an inner lumen for passing the light conducting fiber into the expandable member; and an articular member configured to be attached to the expandable member and having a bearing surface.

In some embodiments, a photodynamic joint spacer includes an expandable member configured for attachment to a bone having an excised region; a formable bar configured for attachment to the bone along at least a portion of the expandable member; and a light-sensitive liquid passed into the expandable member to expand the expandable member, wherein the expandable member is shaped by the formable bar to a shape resembling the excised region of the bone, and wherein the light-sensitive liquid is curable upon exposure to light energy to set the expandable member in the shape resembling the excised region to form a photodynamic joint spacer.

In some embodiments, a system for forming a photodynamic joint spacer includes a delivery catheter having an elongated shaft with a proximal end, a distal end, and a longitudinal axis therebetween, the delivery catheter having an inner void for passing at least one light-sensitive liquid therethrough; an expandable member releasably engaging the distal end of the delivery catheter, the expandable member moveable from a deflated state to an inflated state when the at least one light-sensitive liquid enters the expandable member, wherein the expandable member is sufficiently designed to engage a bone; a formable bar configured for attachment to the bone adjacent the expandable member to shape the expandable member into a desired shape; and a light conducting fiber for providing light energy to the light-sensitive liquid within the expandable member to cure the light-sensitive liquid within the expandable member to set the expandable member in the desired shape to form a photodynamic joint spacer.

In some embodiments, a method for stabilizing an articular joint includes attaching a formable bar to a bone in proximity to an excised region; disposing an expandable member adjacent to the formable member; shaping, with the formable bar, the expandable member to approximate an anatomical angle of the excised region of the bone; expanding the expandable member with a light-sensitive liquid; and curing the light-sensitive liquid within the expandable member to create a photodynamic joint spacer having the anatomical angle of the excised region of the bone to stabilize the joint. In some embodiments, to the expandable member to the bone, the expandable member may be inserted into an intramedullary cavity of the bone.

In some embodiments, a method for stabilizing an articular joint that includes inserting an expandable member into a cavity through a joint such that a first end of the expandable member is positioned in a first bone on one side of the joint and a second end of the expandable member is inserted into a second bone on the opposite side of the joint; expanding the expandable member with a light-sensitive liquid; and curing the light-sensitive liquid within the expandable member to fuse the joint.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A photodynamic joint spacer comprising:
an expandable member configured for attachment to a bone having an excised region;
a formable bar configured for attachment to the bone along at least a portion of the expandable member; and
a light-sensitive liquid passed into the expandable member to expand the expandable member, wherein the expandable member is shaped by the formable bar to a shape resembling the excised region of the bone, and
wherein the light-sensitive liquid is curable upon exposure to light energy to set the expandable member in the shape resembling the excised region of the bone to form a photodynamic joint spacer.

2. The photodynamic joint spacer of claim 1, wherein the formable bar conforms to an outer surface of the bone.

3. The photodynamic joint spacer of claim 1, wherein the formable bar is semi-cylindrical for conformal attachment of the formable bar to an outer surface of the bone.

4. The photodynamic joint spacer of claim 1, wherein the expandable member is insertable into an intramedullary cavity of the bone.

5. The photodynamic joint spacer of claim 1 further comprising an inner lumen in the expandable member to provide kink resistance to the expandable member.

6. The photodynamic joint spacer of claim 1 further comprising an inner lumen in the expandable member for insertion of a light conducting fiber into the expandable member for providing light energy to the light-sensitive liquid.

7. The photodynamic joint spacer of claim 1 further comprising retaining members for attaching the expandable member to the formable bar.

8. The photodynamic joint spacer of claim 1, wherein the expandable member is bent by the formable member to a natural angle of the excised region of the bone.

9. The photodynamic joint spacer of claim 1, wherein the formable bar includes a semi-cylindrical shape to assist with a conformal attachment of the formable bar to an outer surface of the bone.

10. The photodynamic joint spacer of claim 1, wherein the formable bar is mounted partially to an internal side of the cavity of the bone, such that a distal end of the expandable member extends outside and beyond the cavity parallel to the formable bar.

11. The photodynamic joint spacer of claim 1, wherein the formable bar is removably attached to the bone, the formable bar is shaped to substantially conform to a surface of the bone to which the formable bar is removably attached.

12. The photodynamic joint spacer of claim 1, wherein the formable bar is configured for attachment to the bone adjacent the expandable member to shape the expandable member.

13. The photodynamic joint spacer of claim 1, wherein the formable bar is one of between 0.5 mm to 4.0 mm thick, between 1.0 cm and 6.0 cm wide, having a length 30.0 cm or more or some combination thereof.

14. The photodynamic joint spacer of claim 1, wherein the light-sensitive liquid is passed into the expandable member to expand the expandable member from a deflated state to an inflated state when the light-sensitive liquid enters the expandable member.

* * * * *